(12) United States Patent
Vock et al.

(10) Patent No.: US 12,419,380 B2
(45) Date of Patent: **\*Sep. 23, 2025**

(54) UNITLESS ACTIVITY ASSESSMENT AND ASSOCIATED METHODS

(71) Applicant: Apple Inc., Cupertino, CA (US)

(72) Inventors: Curtis A. Vock, Niwot, CO (US);
Perry Youngs, Longmont, CO (US)

(73) Assignee: Apple Inc., Cupertino, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/479,656

(22) Filed: Oct. 2, 2023

(65) Prior Publication Data

US 2024/0172835 A1    May 30, 2024

Related U.S. Application Data

(63) Continuation of application No. 17/449,587, filed on Sep. 30, 2021, now Pat. No. 11,786,006, which is a
(Continued)

(51) Int. Cl.
*G08B 21/00*    (2006.01)
*A43B 1/00*    (2006.01)
(Continued)

(52) U.S. Cl.
CPC .............. *A43B 7/00* (2013.01); *A43B 1/0036* (2013.01); *A43B 3/34* (2022.01); *A43B 3/50* (2022.01);
(Continued)

(58) Field of Classification Search
USPC ... 340/540, 693.1, 555, 545.3, 545.4, 545.5, 340/552, 561, 522, 669–670, 686.1,
(Continued)

(56) References Cited

U.S. PATENT DOCUMENTS 3,612,265 A    10/1971  Dickerson
3,769,723 A    11/1973  Masterson et al.
(Continued)

FOREIGN PATENT DOCUMENTS

DE    10325805 A1    1/2005
EP    0336782 A2    10/1989
(Continued)

OTHER PUBLICATIONS

Advisory Action received for U.S. Appl. No. 08/867,083, mailed on Mar. 14, 2000.
(Continued)

*Primary Examiner* — Daniel Previl
(74) *Attorney, Agent, or Firm* — Kubota & Basol LLP

(57) ABSTRACT

A system assesses activity and displays a unitless activity value. A detector senses activity of a user. A processor reads sensed activity data from the detector. A display displays the unitless activity value. An enclosure houses the detector and the processor. The processor periodically reads the sensed activity data from the detector and processes the data to generate an activity number, the number being used to generate the unitless activity value based upon a maximum number and a display range.

20 Claims, 9 Drawing Sheets

Related U.S. Application Data continuation of application No. 16/834,989, filed on Mar. 30, 2020, now Pat. No. 11,140,943, which is a continuation of application No. 16/525,875, filed on Jul. 30, 2019, now Pat. No. 10,645,991, which is a continuation of application No. 15/972,959, filed on May 7, 2018, now Pat. No. 10,376,015, which is a continuation of application No. 15/443,392, filed on Feb. 27, 2017, now Pat. No. 9,968,158, which is a continuation of application No. 14/298,454, filed on Jun. 6, 2014, now Pat. No. 9,578,927, which is a continuation of application No. 13/544,733, filed on Jul. 9, 2012, now Pat. No. 8,749,380, which is a continuation of application No. 13/034,311, filed on Feb. 24, 2011, now Pat. No. 8,217,788, which is a continuation of application No. 12/083,726, filed as application No. PCT/US2006/040970 on Oct. 18, 2006, now Pat. No. 7,911,339.

(60) Provisional application No. 60/728,031, filed on Oct. 18, 2005.

(51) Int. Cl.
| | | |
|---|---|---|
| *A43B 3/34* | (2022.01) | |
| *A43B 3/50* | (2022.01) | |
| *A43B 7/00* | (2006.01) | |
| *A43D 1/00* | (2006.01) | |
| *G01N 33/00* | (2006.01) | |
| *G08B 7/00* | (2006.01) | |
| *G08B 21/18* | (2006.01) | |

(52) U.S. Cl.
CPC ............... *A43D 1/00* (2013.01); *G01N 33/00* (2013.01); *G08B 7/00* (2013.01); *G08B 21/182* (2013.01); *G01N 33/008* (2024.05); *G01N 33/0086* (2024.05)

(58) Field of Classification Search
USPC .............................................. 340/691.2, 692
See application file for complete search history.

(56) References Cited

U.S. PATENT DOCUMENTS

| | | |
|---|---|---|
| 3,807,388 A | 4/1974 | Orr et al. |
| 3,918,058 A | 11/1975 | Noyori et al. |
| 3,958,459 A | 5/1976 | Shimomura |
| 3,978,725 A | 9/1976 | Hadtke |
| 4,089,057 A | 5/1978 | Eriksson |
| 4,101,873 A | 7/1978 | Anderson et al. |
| 4,114,450 A | 9/1978 | Shulman et al. |
| 4,125,801 A | 11/1978 | Leenhouts |
| 4,195,642 A | 4/1980 | Price et al. |
| 4,210,024 A | 7/1980 | Ishiwatari et al. |
| 4,223,211 A | 9/1980 | Allsen et al. |
| 4,248,244 A | 2/1981 | Charnitski et al. |
| 4,317,126 A | 2/1982 | Gragg, Jr. |
| 4,371,188 A | 2/1983 | Hull |
| 4,371,945 A | 2/1983 | Karr et al. |
| 4,375,674 A | 3/1983 | Thornton |
| 4,423,630 A | 1/1984 | Morrison |
| 4,434,801 A | 3/1984 | Jiminez et al. |
| 4,516,110 A | 5/1985 | Overmyer |
| 4,516,865 A | 5/1985 | Hideo |
| 4,566,461 A | 1/1986 | Lubell et al. |
| 4,578,769 A | 3/1986 | Frederick |
| 4,603,698 A | 8/1986 | Guttmann |
| 4,625,733 A | 12/1986 | Saeynaejaekangas |
| 4,649,552 A | 3/1987 | Yukawa |
| 4,694,694 A | 9/1987 | Makancic et al. |
| 4,699,379 A | 10/1987 | Chateau et al. |
| 4,703,445 A | 10/1987 | Dassler |
| 4,720,093 A | 1/1988 | Del Mar |
| 4,722,222 A | 2/1988 | Purdy et al. |
| 4,736,312 A | 4/1988 | Dassler et al. |
| 4,745,564 A | 5/1988 | Tennes et al. |
| 4,757,453 A | 7/1988 | Nasiff |
| 4,757,714 A | 7/1988 | Purdy et al. |
| 4,759,219 A | 7/1988 | Cobb et al. |
| 4,763,275 A | 8/1988 | Carlin |
| 4,763,284 A | 8/1988 | Carlin |
| 4,763,287 A | 8/1988 | Gerhaeuser et al. |
| 4,771,394 A | 9/1988 | Cavanagh |
| 4,774,679 A | 9/1988 | Carlin |
| 4,775,948 A | 10/1988 | Dial et al. |
| 4,780,837 A | 10/1988 | Namekawa |
| 4,821,218 A | 4/1989 | Poetsch |
| 4,822,042 A | 4/1989 | Landsman |
| 4,824,107 A | 4/1989 | French |
| 4,829,812 A | 5/1989 | Parks et al. |
| 4,830,021 A | 5/1989 | Thornton |
| 4,862,394 A | 8/1989 | Thompson et al. |
| 4,862,395 A | 8/1989 | Fey et al. |
| 4,873,867 A | 10/1989 | Mcpherson et al. |
| 4,876,500 A | 10/1989 | Wu |
| 4,883,271 A | 11/1989 | French |
| 4,903,212 A | 2/1990 | Yokouchi et al. |
| 4,935,887 A | 6/1990 | Abdalah et al. |
| 4,955,980 A | 9/1990 | Masuo |
| 5,033,013 A | 7/1991 | Kato et al. |
| 5,036,467 A | 7/1991 | Blackburn et al. |
| 5,056,783 A | 10/1991 | Matcovich et al. |
| 5,067,081 A | 11/1991 | Person |
| 5,088,836 A | 2/1992 | Yamada et al. |
| 5,144,226 A | 9/1992 | Rapp |
| 5,148,002 A | 9/1992 | Kuo et al. |
| 5,150,310 A | 9/1992 | Greenspun et al. |
| 5,162,828 A | 11/1992 | Furness et al. |
| 5,181,181 A | 1/1993 | Glynn |
| 5,200,827 A | 4/1993 | Hanson et al. |
| 5,243,993 A | 9/1993 | Alexander et al. |
| 5,258,927 A | 11/1993 | Havriluk et al. |
| 5,295,085 A | 3/1994 | Hoffacker |
| 5,316,249 A | 5/1994 | Anderson |
| 5,324,038 A | 6/1994 | Sasser |
| 5,335,664 A | 8/1994 | Nagashima |
| 5,339,699 A | 8/1994 | Carignan |
| 5,343,445 A | 8/1994 | Cherdak |
| 5,348,519 A | 9/1994 | Prince et al. |
| 5,382,972 A | 1/1995 | Kannes |
| 5,396,429 A | 3/1995 | Hanchett |
| 5,420,828 A | 5/1995 | Geiger |
| 5,426,595 A | 6/1995 | Picard |
| 5,436,838 A | 7/1995 | Miyamori |
| 5,446,775 A | 8/1995 | Wright et al. |
| 5,450,329 A | 9/1995 | Tanner |
| 5,452,269 A | 9/1995 | Cherdak |
| 5,471,405 A | 11/1995 | Marsh |
| 5,475,725 A | 12/1995 | Nakamura |
| 5,478,006 A | 12/1995 | Taguchi |
| 5,485,402 A | 1/1996 | Smith et al. |
| 5,486,815 A | 1/1996 | Wagner |
| 5,490,068 A | 2/1996 | Shimizu et al. |
| 5,509,082 A | 4/1996 | Toyama et al. |
| 5,513,854 A | 5/1996 | Daver |
| 5,524,637 A | 6/1996 | Erickson |
| 5,526,326 A | 6/1996 | Fekete et al. |
| 5,528,228 A | 6/1996 | Wilk |
| 5,539,336 A | 7/1996 | Nguyen et al. |
| 5,541,604 A | 7/1996 | Meier |
| 5,546,307 A | 8/1996 | Mazur et al. |
| 5,546,974 A | 8/1996 | Bireley |
| 5,564,698 A | 10/1996 | Honey et al. |
| 5,574,669 A | 11/1996 | Marshall |
| 5,583,776 A | 12/1996 | Levi et al. |
| 5,590,908 A | 1/1997 | Carr |
| 5,592,401 A | 1/1997 | Kramer |
| 5,605,336 A | 2/1997 | Gaoiran et al. |
| 5,615,132 A | 3/1997 | Horton et al. |
| 5,617,084 A | 4/1997 | Sears |
| 5,618,995 A | 4/1997 | Otto et al. |

(56) References Cited

U.S. PATENT DOCUMENTS

| | | |
|---|---|---|
| 5,627,548 A | 5/1997 | Woo et al. |
| 5,629,131 A | 5/1997 | De et al. |
| 5,633,070 A | 5/1997 | Murayama et al. |
| 5,636,146 A | 6/1997 | Flentov et al. |
| 5,646,857 A | 7/1997 | Mcburney et al. |
| 5,671,010 A | 9/1997 | Shimbo et al. |
| 5,671,162 A | 9/1997 | Werbin |
| 5,673,691 A | 10/1997 | Abrams et al. |
| 5,688,183 A | 11/1997 | Sabatino et al. |
| 5,690,119 A | 11/1997 | Rytky et al. |
| 5,690,591 A | 11/1997 | Kenmochi et al. |
| 5,690,773 A | 11/1997 | Fidalgo et al. |
| 5,694,340 A | 12/1997 | Kim |
| 5,701,257 A | 12/1997 | Miura et al. |
| 5,720,200 A | 2/1998 | Anderson et al. |
| 5,721,539 A | 2/1998 | Goetzl |
| 5,723,786 A | 3/1998 | Klapman |
| 5,724,265 A | 3/1998 | Hutchings |
| 5,734,337 A | 3/1998 | Kupersmit |
| 5,738,104 A | 4/1998 | Lo et al. |
| 5,743,269 A | 4/1998 | Okigami et al. |
| 5,745,037 A | 4/1998 | Guthrie et al. |
| 5,749,615 A | 5/1998 | Itson |
| 5,754,938 A | 5/1998 | Herz et al. |
| 5,761,096 A | 6/1998 | Zakutin |
| 5,771,485 A | 6/1998 | Echigo |
| 5,779,576 A | 7/1998 | Smith et al. |
| 5,781,155 A | 7/1998 | Woo et al. |
| 5,790,477 A | 8/1998 | Hauke |
| 5,796,338 A | 8/1998 | Mardirossian |
| 5,807,284 A | 9/1998 | Foxlin |
| 5,812,056 A | 9/1998 | Law |
| 5,862,803 A | 1/1999 | Besson et al. |
| 5,886,739 A | 3/1999 | Winningstad |
| 5,891,042 A | 4/1999 | Sham et al. |
| 5,897,457 A | 4/1999 | Mackovjak |
| 5,899,963 A | 5/1999 | Hutchings |
| 5,901,303 A | 5/1999 | Chew |
| 5,905,460 A | 5/1999 | Odagiri et al. |
| 5,914,659 A | 6/1999 | Herman et al. |
| 5,918,281 A | 6/1999 | Nabulsi |
| 5,918,502 A | 7/1999 | Bishop |
| 5,925,001 A | 7/1999 | Hoyt et al. |
| 5,929,335 A | 7/1999 | Carter |
| 5,930,741 A | 7/1999 | Kramer |
| 5,936,523 A | 8/1999 | West |
| 5,946,643 A | 8/1999 | Zakutin |
| 5,947,917 A | 9/1999 | Carte et al. |
| 5,955,667 A | 9/1999 | Fyfe |
| 5,959,568 A | 9/1999 | Woolley |
| 5,960,380 A | 9/1999 | Flentov et al. |
| 5,963,523 A | 10/1999 | Kayama et al. |
| 5,963,891 A | 10/1999 | Walker et al. |
| 5,976,083 A | 11/1999 | Richardson et al. |
| 5,977,877 A | 11/1999 | Mcculloch et al. |
| 5,978,972 A | 11/1999 | Stewart et al. |
| 5,984,842 A | 11/1999 | Chu |
| 6,002,982 A | 12/1999 | Fry |
| 6,009,629 A | 1/2000 | Gnepf et al. |
| 6,011,491 A | 1/2000 | Goetzl |
| 6,013,007 A | 1/2000 | Root et al. |
| 6,018,677 A | 1/2000 | Vidrine et al. |
| 6,018,705 A | 1/2000 | Gaudet et al. |
| 6,020,851 A | 2/2000 | Busack |
| 6,028,617 A | 2/2000 | Sawano et al. |
| 6,028,625 A | 2/2000 | Cannon |
| 6,028,627 A | 2/2000 | Helmsderfer |
| 6,032,084 A | 2/2000 | Anderson et al. |
| 6,032,108 A | 2/2000 | Seiple et al. |
| 6,032,530 A | 3/2000 | Hock |
| 6,043,747 A | 3/2000 | Altenhofen |
| 6,045,364 A | 4/2000 | Dugan et al. |
| 6,052,654 A | 4/2000 | Gaudet et al. |
| 6,057,756 A | 5/2000 | Engellenner |
| 6,059,576 A | 5/2000 | Brann |
| 6,073,086 A | 6/2000 | Marinelli |
| 6,074,271 A | 6/2000 | Derrah |
| 6,075,443 A | 6/2000 | Schepps et al. |
| 6,087,941 A | 7/2000 | Ferraz |
| 6,091,342 A | 7/2000 | Janesch et al. |
| 6,111,541 A | 8/2000 | Karmel |
| 6,111,571 A | 8/2000 | Summers |
| 6,122,340 A | 9/2000 | Darley et al. |
| 6,122,959 A | 9/2000 | Hoshal et al. |
| 6,122,960 A | 9/2000 | Hutchings et al. |
| 6,125,686 A | 10/2000 | Haan et al. |
| 6,127,931 A | 10/2000 | Mohr |
| 6,135,951 A | 10/2000 | Richardson et al. |
| 6,148,271 A | 11/2000 | Marinelli |
| 6,151,647 A | 11/2000 | Sarat |
| 6,157,898 A | 12/2000 | Marinelli |
| 6,160,254 A | 12/2000 | Zimmerman et al. |
| 6,163,021 A | 12/2000 | Mickelson |
| 6,167,356 A | 12/2000 | Squadron et al. |
| 6,183,425 B1 | 2/2001 | Whalen et al. |
| 6,195,921 B1 | 3/2001 | Truong |
| 6,196,932 B1 | 3/2001 | Marsh et al. |
| 6,204,813 B1 | 3/2001 | Wadell et al. |
| 6,212,427 B1 | 4/2001 | Hoover |
| 6,226,622 B1 | 5/2001 | Dabbiere |
| 6,238,338 B1 | 5/2001 | Deluca et al. |
| 6,245,002 B1 | 6/2001 | Beliakov |
| 6,249,487 B1 | 6/2001 | Yano et al. |
| 6,254,513 B1 | 7/2001 | Takenaka et al. |
| 6,263,279 B1 | 7/2001 | Bianco et al. |
| 6,266,623 B1 | 7/2001 | Vock et al. |
| 6,305,221 B1 | 10/2001 | Hutchings |
| 6,356,856 B1 | 3/2002 | Damen et al. |
| 6,357,147 B1 | 3/2002 | Darley et al. |
| 6,360,597 B1 | 3/2002 | Hubbard, Jr. |
| 6,380,597 B1 | 4/2002 | Gudesen et al. |
| 6,385,473 B1 | 5/2002 | Haines et al. |
| 6,436,052 B1 | 8/2002 | Nikolic et al. |
| 6,441,747 B1 | 8/2002 | Khair et al. |
| 6,456,261 B1 | 9/2002 | Zhang |
| 6,459,881 B1 | 10/2002 | Hoder et al. |
| 6,463,385 B1 | 10/2002 | Fry |
| 6,493,652 B1 | 12/2002 | Ohlenbusch et al. |
| 6,498,994 B2 | 12/2002 | Vock et al. |
| 6,499,000 B2 | 12/2002 | Flentov et al. |
| 6,501,393 B1 | 12/2002 | Richards et al. |
| 6,504,483 B1 | 1/2003 | Richards et al. |
| 6,516,284 B2 | 2/2003 | Flentov et al. |
| 6,527,711 B1 | 3/2003 | Stivoric et al. |
| 6,529,131 B2 | 3/2003 | Wentworth |
| 6,531,982 B1 | 3/2003 | White et al. |
| 6,539,336 B1 | 3/2003 | Vock et al. |
| 6,560,903 B1 | 5/2003 | Darley |
| 6,563,417 B1 | 5/2003 | Shaw |
| 6,570,526 B1 | 5/2003 | Noller et al. |
| 6,571,193 B1 | 5/2003 | Unuma et al. |
| 6,582,342 B2 | 6/2003 | Kaufman |
| 6,595,929 B2 | 7/2003 | Stivoric et al. |
| 6,600,418 B2 | 7/2003 | Francis et al. |
| 6,605,038 B1 | 8/2003 | Teller et al. |
| 6,606,556 B2 | 8/2003 | Curatolo et al. |
| 6,611,782 B1 | 8/2003 | Wooster et al. |
| 6,611,789 B1 | 8/2003 | Darley |
| 6,614,349 B1 | 9/2003 | Proctor et al. |
| 6,617,962 B1 | 9/2003 | Horwitz et al. |
| 6,619,835 B2 | 9/2003 | Kita |
| 6,633,743 B1 | 10/2003 | Berlinsky |
| 6,643,608 B1 | 11/2003 | Hershey et al. |
| 6,669,600 B2 * | 12/2003 | Warner .............. A63B 24/0062 482/4 |
| 6,714,121 B1 | 3/2004 | Moore |
| 6,716,139 B1 | 4/2004 | Hosseinzadeh-dolkhani et al. |
| 6,735,630 B1 | 5/2004 | Gelvin et al. |
| 6,748,902 B1 | 6/2004 | Boesch et al. |
| 6,790,178 B1 | 9/2004 | Mault et al. |
| 6,793,607 B2 | 9/2004 | Neil |
| 6,813,586 B1 | 11/2004 | Vock et al. |
| 6,825,777 B2 | 11/2004 | Vock et al. |
| 6,850,252 B1 | 2/2005 | Hoffberg |

(56) References Cited

U.S. PATENT DOCUMENTS

| | | | |
|---|---|---|---|
| 6,856,934 B2 | 2/2005 | Vock et al. | |
| 6,883,694 B2 | 4/2005 | Abelow | |
| 6,885,971 B2 | 4/2005 | Vock et al. | |
| 6,898,550 B1 | 5/2005 | Blackadar et al. | |
| 6,900,732 B2 | 5/2005 | Richards | |
| 6,959,259 B2 | 10/2005 | Vock et al. | |
| 6,963,818 B2 | 11/2005 | Flentov et al. | |
| 6,968,179 B1 | 11/2005 | De Vries | |
| 7,009,517 B2 | 3/2006 | Wood | |
| 7,016,687 B1 | 3/2006 | Holland | |
| 7,020,508 B2 * | 3/2006 | Stivoric | A61B 5/0537 |
| 7,030,735 B2 | 4/2006 | Chen | |
| 7,042,360 B2 | 5/2006 | Light et al. | |
| 7,054,784 B2 | 5/2006 | Flentov et al. | |
| 7,062,225 B2 | 6/2006 | White | |
| 7,064,669 B2 | 6/2006 | Light et al. | |
| 7,072,789 B2 | 7/2006 | Vock et al. | |
| 7,092,846 B2 | 8/2006 | Vock et al. | |
| 7,171,331 B2 | 1/2007 | Vock et al. | |
| 7,174,227 B2 | 2/2007 | Kobayashi et al. | |
| 7,174,277 B2 | 2/2007 | Vock et al. | |
| 7,200,517 B2 | 4/2007 | Darley et al. | |
| 7,219,067 B1 | 5/2007 | Mcmullen et al. | |
| 7,251,454 B2 | 7/2007 | White | |
| 7,278,966 B2 | 10/2007 | Hjelt et al. | |
| 7,285,090 B2 | 10/2007 | Stivoric et al. | |
| 7,292,867 B2 | 11/2007 | Werner et al. | |
| 7,299,195 B1 | 11/2007 | Tawakol et al. | |
| 7,454,002 B1 | 11/2008 | Gardner et al. | |
| 7,455,621 B1 * | 11/2008 | Anthony | A63B 24/0062 482/3 |
| 7,519,327 B2 | 4/2009 | White | |
| 7,618,345 B2 | 11/2009 | Corbalis et al. | |
| 7,670,263 B2 | 3/2010 | Ellis et al. | |
| 7,874,841 B1 | 1/2011 | Lycas | |
| 7,911,339 B2 | 3/2011 | Vock et al. | |
| 8,217,788 B2 | 7/2012 | Vock et al. | |
| 8,749,380 B2 | 6/2014 | Vock et al. | |
| 9,165,117 B2 * | 10/2015 | Teller | A61B 5/11 |
| 9,578,927 B2 | 2/2017 | Vock et al. | |
| 9,968,158 B2 | 5/2018 | Vock et al. | |
| 10,376,015 B2 * | 8/2019 | Vock | A43B 3/34 |
| 10,645,991 B2 * | 5/2020 | Vock | G08B 21/182 |
| 11,140,943 B2 * | 10/2021 | Vock | A43D 1/00 |
| 11,786,006 B2 * | 10/2023 | Vock | G08B 7/00 340/540 |
| 2001/0049890 A1 | 12/2001 | Hirsch et al. | |
| 2002/0070862 A1 | 6/2002 | Francis et al. | |
| 2002/0077784 A1 | 6/2002 | Vock et al. | |
| 2002/0107033 A1 | 8/2002 | Kim | |
| 2002/0121975 A1 | 9/2002 | Struble et al. | |
| 2003/0014210 A1 | 1/2003 | Vock et al. | |
| 2003/0050211 A1 | 3/2003 | Hage et al. | |
| 2003/0065805 A1 | 4/2003 | Barnes | |
| 2003/0093248 A1 | 5/2003 | Vock et al. | |
| 2003/0097878 A1 | 5/2003 | Farringdon et al. | |
| 2003/0163287 A1 | 8/2003 | Vock et al. | |
| 2004/0104845 A1 | 6/2004 | Mccarthy | |
| 2004/0177531 A1 | 9/2004 | Dibenedetto et al. | |
| 2004/0253642 A1 | 12/2004 | Zimmermann et al. | |
| 2005/0113650 A1 * | 5/2005 | Pacione | A61B 5/165 600/300 |
| 2005/0113703 A1 * | 5/2005 | Farringdon | A61B 5/021 600/509 |
| 2005/0172311 A1 | 8/2005 | Hjelt et al. | |
| 2005/0177929 A1 | 8/2005 | Greenwald et al. | |
| 2006/0030335 A1 | 2/2006 | Zellner et al. | |
| 2006/0152377 A1 | 7/2006 | Beebe et al. | |
| 2007/0011919 A1 | 1/2007 | Case | |
| 2008/0129735 A1 | 6/2008 | Buck | |
| 2009/0267783 A1 | 10/2009 | Vock et al. | |
| 2011/0140890 A1 | 6/2011 | Vock et al. | |
| 2013/0021152 A1 | 1/2013 | Vock et al. | |
| 2014/0288856 A1 | 9/2014 | Vock et al. | |
| 2017/0164684 A1 | 6/2017 | Vock et al. | |
| 2018/0249783 A1 | 9/2018 | Vock et al. | |
| 2019/0350306 A1 | 11/2019 | Vock et al. | |
| 2020/0221817 A1 | 7/2020 | Vock et al. | |
| 2022/0160074 A1 | 5/2022 | Vock et al. | |

FOREIGN PATENT DOCUMENTS

| | | |
|---|---|---|
| EP | 0917893 B1 | 2/2002 |
| EP | 1292217 B1 | 11/2005 |
| EP | 1292218 B1 | 4/2006 |
| GB | 1567238 A | 5/1980 |
| GB | 2137363 A | 10/1984 |
| JP | H03-152469 A | 6/1991 |
| JP | 2000-122044 A | 4/2000 |
| JP | 2001-321202 A | 11/2001 |
| JP | 2002-101908 A | 4/2002 |
| WO | 1998/06466 A2 | 2/1998 |
| WO | 1998/54581 A2 | 12/1998 |
| WO | 2000/51259 A1 | 8/2000 |
| WO | 2000/078170 A1 | 12/2000 |
| WO | 2001/001706 A1 | 1/2001 |
| WO | 2002/093272 A1 | 11/2002 |

OTHER PUBLICATIONS

Advisory Action received for U.S. Appl. No. 10/234,660, mailed on Jan. 27, 2004, 3 pages.
Advisory Action received for U.S. Appl. No. 10/921,743, mailed on Nov. 25, 2005, 3 pages.
Advisory Action received for U.S. Appl. No. 10/950,897, mailed Nov. 25, 2005, 3 pages.
Advisory Action received for U.S. Appl. No. 08/764,758 mailed on Apr. 29, 1999, 4 pages.
Amendment filed for U.S. Appl. No. 10/234,660, on Jul. 20, 2004.
Amendment response to Office Action for U.S. Appl. No. 08/867,083, mailed on Jun. 26, 2000, 5 pages.
Amendment to Notice of Allowance for U.S. Appl. No. 10/950,897, mailed Dec. 13, 2005.
Appeal Brief filed for U.S. Appl. No. 10/234,660, on Jun. 14, 2004.
Appeal Brief for U.S. Appl. No. 09/089,232, mailed on Jan. 2, 2002.
Appeal Brief for U.S. Appl. No. 09/089,232, mailed on Jul. 26, 2002.
Civil Action No. 05-CV-02323, Complaint, Nov. 16, 2005.
Civil Action No. 06-CV-01100-WDM-PAC, Complaint, Jun. 8, 2000.
Civil Action No. 06-CV-01100-WDM-PAC, Defendants Polar Electro Inc.'s and Polar Electro Oy's Answer and Affirmative Defenses: Polar Electro Inc.'s Counterclaim and Demand for Jury Trial, Jun. 29, 2006, 8 pages.
Civil Action No. 06-CV-01447 MSK-BNB, Answer, Affirmative Defenses, Counterclaims and Demand for Jury Trial, Timex, Sep. 26, 2006, 14 pages.
Civil Action No. 06-CV-01447 MSK-BNB, First Amended Complaint, Aug. 16, 2006, 6 pages.
Civil Action No. 06-CV-01447-MSK-BNB, Complaint, Jul. 26, 2006.
Civil Action No. 06-CV-01447-MSK-BNB, Answer, Affirmative Defenses, Counterclaim, and Demand for Jury Trial, Garmin, Sep. 26, 2006, 11 pages.
Civil Action No. 06-CV-01447-MSK-BNB, Garmin Disclosure Statement, Sep. 26, 2006, 2 pages.
Civil Action No. 06-CV-01447-MSK-BNB, PhatRat Technology, Inc.'s Supplemental Answers and Objections to Defendant, Timex Corporation's Interrogatories Nos. 1, 2, 5, 7-11, 13 and 15, Feb. 12, 2007, 24 pages.
Civil Action No. 06-CV-01447-MSK-BNB, Timex Disclosure Statement, Sep. 26, 2006, 3 pages.
Civil Action No. 06-CV-02122-REB-MJW, Complaint, Oct. 24, 2006.
Civil Action No. 06-CV-02122-REB-MJW, Apple Computer, Inc's Answer to Complaint and Counterclaims, Jan. 22, 2007, 7 pages.
Civil Action No. 07-CV-00078-MSK-BNB, Complaint, Jan. 12, 2007.

(56) References Cited

OTHER PUBLICATIONS

Civil Action No. 07-CV-00078-MSK-BNB, Answer, Feb. 9, 2007, 9 pages.
Civil Action No. 07-CV-00238, Nike Inc.'s Answer, Affirmative Defenses to First Complaint, Mar. 19, 2007, 10 pages.
Civil Action No. 07-CV-00238-REB, Apple Inc.'s Answer to Complaint, Counterclaims and Jury Demand, Mar. 19, 2007, 12 pages.
Civil Action No. 07-CV-00238-REB-PAC, Complaint, Mar. 19, 2007.
Comments on Allowance for U.S. Appl. No. 09/089,232, mailed on Oct. 16, 2002, 1 page.
Ever Forget to Bring Your Cell Phone or Keys?, Catalog Page, PI Manufacturing Corp, 20732 Currier Rd., Walnut, CA 91789, Home Office Accessory, Catalog Nos. TA-100N; TA-100M; TA-100F, US.
Examiner Initiated Interview Summary received for U.S. Appl. No. 09/992,966, mailed on Oct. 27, 2003, 2 pages.
Final Office Action received for U.S. Appl. No. 09/886,578, mailed on Jun. 5, 2002, 13 pages.
Final Office Action received for U.S. Appl. No. 09/992,966 mailed on Jan. 6, 2004, 11 pages.
Final Office Action received for U.S. Appl. No. 09/992,966, mailed on Feb. 3, 2003, 12 pages.
Final Office Action received for U.S. Appl. No. 10/601,208, mailed on May 11, 2005, 8 pages.
Final Office Action received for U.S. Appl. No. 10/601,208, mailed on Sep. 26, 2006, 16 pages.
Final Office Action received for U.S. Appl. No. 10/921,743, mailed on Sep. 13, 2005, 16 pages.
Final Office Action received for U.S. Appl. No. 11/646,768, mailed on Oct. 29, 2007, 8 pages.
Final Office Action received for U.S. Appl. No. 08/867,083, mailed on Jan. 3, 2000, 24 pages.
Final Office Action received for U.S. Appl. No. 09/089,232, mailed on Aug. 8, 2001, 10 pages.
Final Office Action received for U.S. Appl. No. 09/848,445, mailed on May 6, 2004, 7 pages.
Final Office Action received for U.S. Appl. No. 17/449,587, mailed on May 3, 2023, 8 pages.
Final Office Action received U.S. Appl. No. 10/234,660, mailed on Oct. 31, 2003, 11 pages.
GPS Locator for Children, Klass Kids Foundation, Jul. 15, 2014.
Information Disclosure Statement for U.S. Appl. No. 09/089,232 mailed on Oct. 23, 1998, 2 pages.
International Preliminary Examination Report received for PCT Application No. PCT/US2000/018237, mailed on Oct. 9, 2003, 3 pages.
International Search Report received for PCT Patent Application No. PCT/US1998/011268, mailed on Jan. 11, 1999, 2 pages.
International Search Report received for PCT Patent Application No. PCT/US2000/018237, mailed on Oct. 17, 2000, 1 page.
International Search Report received for PCT Patent Application No. PCT/US2001/051620, mailed on Sep. 25, 2002, 1 page.
International Search Report received for PCT Patent International Application No. PCT/US2006/040970, mailed on Jun. 22, 2007, 5 pages.
Marked up Claims by USPTO for U.S. Appl. No. 10/234,660, on Jul. 28, 2004.
Non-Final Office Action received for U.S. Appl. No. 09/992,966, mailed on Jul. 18, 2003, 16 pages.
Non-Final Office Action received for U.S. Appl. No. 09/992,966, mailed on Mar. 28, 2002, 18 pages.
Non-Final Office Action received for U.S. Appl. No. 10/297,270, mailed on Dec. 13, 2004, 13 pages.
Non-Final Office Action received for U.S. Appl. No. 10/297,270, mailed on Feb. 9, 2006, 13 pages.
Non-Final Office Action received for U.S. Appl. No. 10/297,270, mailed on Jan. 11, 2007, 14 pages.
Non-Final Office Action received for U.S. Appl. No. 10/297,270, mailed on Jul. 13, 2005, 16 pages.
Non-Final Office Action received for U.S. Appl. No. 10/297,270, mailed on Jul. 26, 2007, 14 pages.
Non-Final Office Action received for U.S. Appl. No. 10/297,270, mailed on Sep. 25, 2006, 13 pages.
Non-Final Office Action received for U.S. Appl. No. 10/297,270, on Jul. 29, 2004, 28 pages.
Non-Final Office Action received for U.S. Appl. No. 10/601,208, mailed on Aug. 26, 2004, 7 pages.
Non-Final Office Action received for U.S. Appl. No. 10/601,208, mailed on Feb. 15, 2006, 13 pages.
Non-Final Office Action received for U.S. Appl. No. 10/842,947, mailed on Jun. 30, 2005, 7 pages.
Non-Final Office Action received for U.S. Appl. No. 10/842,947, mailed on Nov. 30, 2004, 6 pages.
Non-Final Office Action received for U.S. Appl. No. 10/921,743, mailed on Mar. 4, 2005, 9 pages.
Non-Final Office Action received for U.S. Appl. No. 10/921,743, mailed on May 26, 2005, 8 pages.
Non-Final Office Action received for U.S. Appl. No. 10/950,897, mailed Jun. 23, 2005, 7 pages.
Non-Final Office Action received for U.S. Appl. No. 10/950,897, mailed Mar. 7, 2005, 7 pages.
Non-Final Office Action received for U.S. Appl. No. 10/950,897, mailed Sep. 9, 2005, 8 pages.
Non-Final Office Action received for U.S. Appl. No. 11/221,029, mailed on Sep. 8, 2006, 8 pages.
Non-Final Office Action received for U.S. Appl. No. 11/358,508, mailed on Aug. 14, 2006, 8 pages.
Non-Final Office Action received for U.S. Appl. No. 11/434,588, mailed on Jan. 31, 2007, 10 pages.
Non-Final Office Action received for U.S. Appl. No. 11/747,081, mailed on Jan. 24, 2008, 12 pages.
Non-Final Office Action received for U.S. Appl. No. 09/698,659, mailed on Mar. 19, 2002, 5 pages.
Non-Final Office Action received for U.S. Appl. No. 09/698,659, mailed on Nov. 21, 2002, 6 pages.
Non-Final Office Action received for U.S. Appl. No. 09/848,445, mailed on Dec. 5, 2003, 9 pages.
Non-Final Office Action received for U.S. Appl. No. 09/886,578, mailed on Nov. 8, 2001, 13 pages.
Non-Final Office Action received for U.S. Appl. No. 11/746,863, mailed on Mar. 26, 2009, 22 pages.
Non-Final Office Action received for U.S. Appl. No. 12/083,726, mailed on Aug. 9, 2010, 8 pages.
Non-Final Office Action received for U.S. Appl. No. 13/544,733, mailed on Mar. 25, 2013, 10 pages.
Non-Final Office Action received for U.S. Appl. No. 13/544,733, mailed on Sep. 5, 2013, 9 pages.
Non-Final Office Action received for U.S. Appl. No. 14/298,454, mailed on May 5, 2016, 9 pages.
Non-Final Office Action received for U.S. Appl. No. 15/443,392, mailed on Jun. 22, 2017, 12 pages.
Non-Final Office Action received for U.S. Appl. No. 15/972,959, mailed on Nov. 14, 2018, 8 pages.
Non-Final Office Action received for U.S. Appl. No. 16/525,875, mailed on Oct. 3, 2019, 8 pages.
Non-Final Office Action received for U.S. Appl. No. 16/834,989, mailed on Feb. 16, 2021, 8 pages.
Non-Final Office Action received for U.S. Appl. No. 17/449,587, mailed on Nov. 23, 2022, 10 pages.
Non-Final Office Action received U.S. Appl. No. 10/234,660, mailed on Mar. 31, 2003, 12 pages.
Non-Final Office Action received U.S. Appl. No. 11/598,410, mailed on Jun. 13, 2007, 8 pages.
Non-Final Office Action received U.S. Appl. No. 11/646,768, mailed on May 7, 2007, 8 pages.
Notice of Allowability & Examiner Interview Summary received for U.S. Appl. No. 11/358,508, mailed on Oct. 18, 2006, 9 pages.
Notice of Allowability received U.S. Appl. No. 11/598,410, mailed on Sep. 26, 2007, 1 page.
Notice of Allowance and Examiner Interview Summary received U.S. Appl. No. 11/484,199, mailed on Oct. 6, 2006, 10 pages.

(56) References Cited

OTHER PUBLICATIONS

Notice of Allowance received for U.S. Appl. No. 09/886,578 mailed on Sep. 9, 2002.
Notice of Allowance received for U.S. Appl. No. 10/950,897, mailed Feb. 13, 2005.
Notice of Allowance received for U.S. Appl. No. 09/992,966, mailed on Apr. 15, 2004, 5 pages.
Notice of Allowance received for U.S. Appl. No. 10/234,660, on Aug. 2, 2004, 3 pages.
Notice of Allowance received for U.S. Appl. No. 10/601,208, mailed on Dec. 8, 2006, 4 pages.
Notice of Allowance received for U.S. Appl. No. 10/842,947, mailed on Feb. 9, 2006, 3 pages.
Notice of Allowance received for U.S. Appl. No. 10/921,743, mailed Feb. 16, 2006, 3 pages.
Notice of Allowance received for U.S. Appl. No. 11/221,029, mailed on Oct. 3, 2006, 4 pages.
Notice of Allowance received for U.S. Appl. No. 11/252,576, mailed on Dec. 11, 2007, 14 pages.
Notice of Allowance received for U.S. Appl. No. 11/434,588, mailed on Jul. 11, 2007, 6 pages.
Notice of Allowance received for U.S. Appl. No. 11/646,768, mailed on Jan. 18, 2008, 9 pages.
Notice of Allowance received for U.S. Appl. No. 08/764,758 mailed on Jun. 1, 1999, 4 pages.
Notice of Allowance received for U.S. Appl. No. 08/867,083, mailed on Feb. 6, 2001.
Notice of Allowance received for U.S. Appl. No. 09/089,232, mailed on Oct. 2, 2002.
Notice of Allowance received for U.S. Appl. No. 11/434,588, mailed on Nov. 6, 2007, 4 pages.
Notice of Allowance received for U.S. Appl. No. 12/083,726 mailed on Nov. 18, 2010, 4 pages.
Notice of Allowance received for U.S. Appl. No. 13/034,311 mailed on Feb. 23, 2012, 5 pages.
Notice of Allowance received for U.S. Appl. No. 13/034,311 mailed on Nov. 17, 2011, 5 pages.
Notice of Allowance received for U.S. Appl. No. 13/034,311 mailed on Sep. 29, 2011, 8 pages.
Notice of Allowance received for U.S. Appl. No. 13/544,733. mailed on Feb. 4, 2014, 5 pages.
Notice of Allowance received for U.S. Appl. No. 14/298,454 mailed on Oct. 24, 2016, 8 pages.
Notice of Allowance received for U.S. Appl. No. 15/443,392, mailed on Jan. 12, 2008, 8 Pages.
Notice of Allowance received for U.S. Appl. No. 15/972,959, mailed on Apr. 10, 2019, 8 pages.
Notice of Allowance received for U.S. Appl. No. 16/525,875 mailed on Dec. 26, 2019, 8 pages.
Notice of Allowance received for U.S. Appl. No. 09/698,659, mailed on Apr. 9, 2003, 4 pages.
Notice of Allowance received for U.S. Appl. No. 16/834,989, mailed on Jun. 9, 2021, 8 pages.
Notice of Allowance received for U.S. Appl. No. 17/449,587, mailed on Jun. 13, 2023, 8 pages.
Notice of Allowance received U.S. Appl. No. 09/992,966, mailed on Sep. 3, 2004, 4 pages.
Notice of Appeal received for U.S. Appl. No. 08/867,083, mailed on Jan. 3, 2000.
Notice of Appeal received for U.S. Appl. No. 09/089,232, mailed on Nov. 5, 2001, 1 page.
Notice of Appeal received for U.S. Appl. No. 09/089,232, mailed on Nov. 7, 2001.
Notice of Appeal Response to Office Action for U.S. Appl. No. 08/867,083, mailed on Jan. 3, 2000, 2 pages.
Notice of Non Compliance Amendment for U.S. Appl. No. 11/358,508, mailed on Sep. 12, 2006, 2 pages.
Office Action received for U.S. Appl. No. 08/867,083, mailed on Jun. 26, 2000, 13 pages.
Office Action received for U.S. Appl. No. 08/764,758 mailed on Aug. 21, 1997, 16 pages.
Office Action received for U.S. Appl. No. 08/764,758 mailed on Dec. 15, 1998, 14 pages.
Office Action received for U.S. Appl. No. 08/764,758 mailed on May 8, 1998, 5 pages.
Office Action received for U.S. Appl. No. 08/867,083 mailed on Apr. 8, 1999, 23 pages.
Office Action received for U.S. Appl. No. 09/089,232, mailed on Apr. 26, 2002.
Office Action received for U.S. Appl. No. 09/089,232, mailed on Dec. 19, 2000, 10 pages.
Office Action received for U.S. Appl. No. 09/089,232, mailed on Jan. 27, 2003.
Office Action received for U.S. Appl. No. 09/089,232, mailed on May 30, 2000, 16 pages.
Office Action received for U.S. Appl. No. 09/089,232, mailed on Nov. 27, 1998, 9 pages.
Preliminary Amendment filed for U.S. Appl. No. 10/601,208, mailed on Jun. 20, 2003.
Preliminary Amendment for U.S. Appl. No. 10/842,947, mailed on May 11, 2004.
Preliminary Amendment for U.S. Appl. No. 11/221,029, mailed on Aug. 22, 2006.
Preliminary Amendment for U.S. Appl. No. 11/358,508, mailed on Jul. 26, 2006.
Preliminary Amendment for U.S. Appl. No. 11/358,508, mailed on Mar. 30, 2006.
Preliminary Amendment for U.S. Appl. No. 11/358,508, mailed on May 30, 2006, 8 pages.
Preliminary Amendment for U.S. Appl. No. 11/484,199, mailed on Sep. 7, 2006, 4 pages.
Preliminary Amendment for U.S. Appl. No. 09/848,445, mailed on Dec. 5, 2001.
Preliminary Amendment for U.S. Appl. No. 09/886,578, mailed on Jun. 21, 2001.
Preliminary Amendment response to Office Action for U.S. Appl. No. 09/089,232 mailed on May 30, 2000, 8 pages.
Request Deletion of Named Inventors Pursuant to 37 CFR § 1.63 (d)(2) received by the Patent Office for U.S. Appl. No. 10/297,270, mailed on Oct. 4, 2002.
Requirement for Restriction/Election received for U.S. Appl. No. 10/601,208, mailed on Jun. 15, 2004, 3 pages.
Response to Notice for U.S. Appl. No. 11/358,508, mailed on Sep. 12, 2006.
Response to Office Action & Advisory Action for U.S. Appl. No. 10/921,743, received on Sep. 13, 2005 & Nov. 25, 2005 respectively, 10 pages.
Response to Office Action (Rule 116) for U.S. Appl. No. 09/848,445, mailed on May 6, 2004, 4 pages.
Response to Office Action for U.S. Appl. No. 09/992,966 mailed on Feb. 3, 2003.
Response to Office Action for U.S. Appl. No. 09/992,966 mailed on Mar. 28, 2002.
Response to Office Action for U.S. Appl. No. 09/992,966 mailed on Jan. 6, 2004, 8 pages.
Response to Office Action for U.S. Appl. No. 10/601,208, mailed on Jun. 15, 2004.
Response to Office Action for U.S. Appl. No. 10/842,947, mailed on Jun. 30, 2005.
Response to Office Action for U.S. Appl. No. 10/842,947, mailed on Nov. 30, 2004.
Response to Office Action for U.S. Appl. No. 10/950,897, mailed Sep. 9, 2005.
Response to Office Action for U.S. Appl. No. 11/221,029, mailed on Sep. 8, 2006.
Response to Office Action for U.S. Appl. No. 11/358,508, mailed on Aug. 14, 2006.
Response to Office Action for U.S. Appl. No. 11/434,588, mailed on Jan. 31, 2007.
Response to Office Action for U.S. Appl. No. 09/886,578, mailed on Jun. 5, 2002, 34 pages.

(56) References Cited

OTHER PUBLICATIONS

Response to Office Action for U.S. Appl. No. 09/886,578, mailed on Nov. 8, 2001, 37 pages.
Response to Office Action for U.S. Appl. No. 09/992,966, mailed on Jul. 18, 2003, 14 pages.
Response to Office Action for U.S. Appl. No. 10/234,660, mailed on Oct. 31, 2003, 11 pages.
Response to Office Action for U.S. Appl. No. 10/297,270, mailed on Dec. 13, 2004, 13 pages.
Response to Office Action for U.S. Appl. No. 10/297,270, mailed on Feb. 9, 2006, 14 pages.
Response to Office Action for U.S. Appl. No. 10/297,270, mailed on Jan. 11, 2007, 21 pages.
Response to Office Action for U.S. Appl. No. 10/297,270, mailed on Jul. 13, 2005, 10 pages.
Response to Office Action for U.S. Appl. No. 10/297,270, mailed on Jul. 26, 2007, 23 pages.
Response to Office Action for U.S. Appl. No. 10/297,270, mailed on Sep. 25, 2006, 15 pages.
Response to Office Action for U.S. Appl. No. 10/297,270, received on Jul. 29, 2004, 12 pages.
Response to Office Action for U.S. Appl. No. 10/601,208, mailed on Aug. 26, 2004, 11 pages.
Response to Office Action for U.S. Appl. No. 10/601,208, mailed on Feb. 15, 2006, 13 pages.
Response to Office Action for U.S. Appl. No. 10/601,208, mailed on May 11, 2005, 10 pages.
Response to Office Action for U.S. Appl. No. 10/601,208, mailed on Sep. 26, 2006, 11 pages.
Response to Office Action for U.S. Appl. No. 10/921,743, mailed on Mar. 4, 2005, 7 pages.
Response to Office Action for U.S. Appl. No. 10/921,743, mailed on May 26, 2005, 9 pages.
Response to Office Action for U.S. Appl. No. 10/950,897, mailed Jun. 23, 2005, 10 pages.
Response to Office Action for U.S. Appl. No. 10/950,897, mailed Nov. 25, 2005, 7 pages.
Response to Office Action for U.S. Appl. No. 11/646,768, mailed on May 7, 2007, 14 pages.
Response to Office Action for U.S. Appl. No. 11/646,768, mailed on Oct. 29, 2007, 4 pages.
Response to Office Action for U.S. Appl. No. 08/867,083, mailed on Apr. 8, 1999, 25 pages.
Response to Office Action for U.S. Appl. No. 09/089,232, mailed on Dec. 19, 2000, 9 pages.
Response to Office Action for U.S. Appl. No. 09/698,659, mailed on Mar. 19, 2002, 6 pages.
Response to Office Action for U.S. Appl. No. 09/698,659, mailed on Nov. 21, 2002, 4 pages.
Response to Office Action for U.S. Appl. No. 09/848,445, mailed on Dec. 5, 2003, 13 pages.
Response to Office Action received for U.S. Appl. No. 10/950,897, mailed Mar. 7, 2005, 10 pages.
Response to Office Action received for U.S. Appl. No. 08/764,758 mailed on Aug. 21, 1997, 25 pages.
Response to Office Action received for U.S. Appl. No. 08/764,758 mailed on May 8, 1998, 5 pages.
Response to Office Action received for U.S. Appl. No. 08/764,758, mailed on Dec. 15, 1998, 14 pages.
Response to Office Action U.S. Appl. No. 10/234,660, mailed on Mar. 31, 2003, 17 pages.
Response to Office Action U.S. Appl. No. 11/598,410, mailed on Jun. 13, 2007, 8 pages.
Restriction Requirement received for U.S. Appl. No. 12/083,726, mailed on Jun. 18, 2010, 6 pages.
Rule 116 Amendment received for U.S. Appl. No. 08/764,758, mailed on Apr. 8, 1999, 5 pages.
Rule 116 Amendment received for U.S. Appl. No. 08/764,758, mailed on May 13, 1999, 3 pages.
Rule 312 Amendment for U.S. Appl. No. 11/358,508, mailed on Oct. 24, 2006.
Second Response to Office Action for U.S. Appl. No. 10/601,208, mailed on Aug. 26, 2004.
Supplemental Response to Office Action for U.S. Appl. No. 08/867,083, mailed on Apr. 8, 1999, 5 pages.
Supplementary European Search Report received for European Patent Application No. 98928854.3 mailed on Feb. 18, 2002, 7 pages.
The GPS Connection, Popular Mechanics, Feb. 2001, p. 65.
Wireless Temperature Monitor, www.echo-on.net/mob/, Nov. 20, 2000.
Your Next . . . , Newsweek, US, Jun. 25, 2001, p. 52.
Cole George, "The Little Label with an Explosion of Applications", Financial Times, Ltd., 2002, pp. 1-3.
Deem, "Fast Forward Go for a Ride on the World's Fastest Sailboat", Popular Mechanics, www.popularmechanics.com, Feb. 2001, pp. 1-2.
Desmarais et al., "How to select and use the right temperature", www.sensorsmag.com, Jan. 2001, pp. 30-36.
Desmarais, "Solutions in Hand", BEI Technologies, Inc., www.sensormag.com, Jan. 2001, pp. 1-2.
Gerhauser et al., "The 'Electronic Shoe' for Jogging", Sports and Recoalescence, IEEE, 1989, 3 pages.
Henkel, "Research & Developments", Sensors, Nov. 2000, paqe 18.
Janssens et al., "Columbus: A Novel Sensor System for Domestic Washing Machines", Sensors Magazine Online, Jun. 2002, pp. 1-9.
Licking, "This is the Future of Medicine", Special Report: E-Health, Business Week E.Biz, Dec. 11, 2000, pp. 77-78.
Li-Ron, "Tomorrow's Cures", Health & Fitness Special Section Online, Newsweek, Dec. 10, 2001, pp. 3-10.
Martella, "Temperature Monitoring System", Product News, Nov. 2000, p. 77.
Nobbe, "Olympic Athletes Get a Boost from Technology", Machine Design, vol. 60, No. 19, Aug. 25, 1988.
Paradiso et al., "Design and Implementation of Expressive Footwear", IBM Systems Journal, vol. 39, Nos. 3&4, May 12, 2000, pp. 511-529.
Paradiso et al., "Instrumented Footwear for Interactive Dance", Version 1.1, Presented at the XII Colloquium on Musical Informatics, Gorizia, Italy, Sep. 24-26, 1998, pp. 1-4.
Sellers, "Gear to Go", Mitch Mandel Photography, Mar. 2001, pp. 61-62.
Shannon et al., "Weighing Scales Based on Low-Power Strain-Gauge Circuits", NASA Tech Briefs, Jun. 2001, p. 49.
Sharp, "A Sense of the Real World", www.idsystems.com/reader/2000_09/sens0900.htm, Sep. 2000, 4 pages.
Skaloud et al., "DGPS-Calibrated Accelerometric System for Dynamic Sports Events", ION GPS 2000, Sep. 19-22, 2000.
Smith et al., "Flexible and Survivable Non-Volatile Memory Data Recorder", AFRL Technology Horizons, Dec. 2000, p. 26.
Webster's II, "New Riverside University Dictionary", The Riverside Publishing Company, 1988, p. 1138.
WarmMark Time Temperature Indicators, www.coldice.com/warmmark temperature indicators.html, Cold Ice., Inc., 4 pages.
Mark of Fitness Flyer, High Quality, Self-Taking Blood Pressure Monitors, Shrewsbury, NJ, US, 4 pages.
Neogen, 3M MonitorMark Time Temperature Indicator, Available online at: <https://www.neogen.com/categories/microbiology/monitormark-time-temperature-indicator?utm_medium=redirect &utm_source=vanity-url&utm_campaign=www.3m.com/3M/en_US/p/d/b00003869/>, 3 pages.
Wysocki, Jr., Do Devices Measuring Body Signs Appeal to the Sick or Healthy, Staff Reporter, Pittsburgh, US, 2 pages.
WarmMark Time Temperature Indicators, www.coldice.com/warmmark temperature indicators.html, Cold Ice., Inc., [retrieved on Jul. 18, 2008], 4 pages.
Mark of Fitness Flyer, High Quality, Self-Taking Blood Pressure Monitors, Shrewsbury, NJ, US, [retrieved on Jul. 18, 2008], 4 pages.
Neogen, 3M MonitorMark Time Temperature Indicator, Available

(56) References Cited

OTHER PUBLICATIONS online at: <https://www.neogen.com/categories/microbiology/monitormark-time-temperature-indicator?utm_medium=redirect&utm_source=vanity-url&utm_campaign=www.3m.com/3M/en_US/p/d/b00003869/>, [retrieved on Jan. 8, 2025], 3 pages.
Wysocki, Jr., Do Devices Measuring Body Signs Appeal to the Sick or Healthy, Staff Reporter, Pittsburgh, US, [retrieved on Jul. 18, 2008], 2 pages.

\* cited by examiner

UNITLESS ACTIVITY ASSESSMENT AND ASSOCIATED METHODS

CROSS-REFERENCE TO RELATED APPLICATIONS

This application is a continuation of U.S. patent application Ser. No. 17/449,587 (now U.S. Publication No. 2022/0160074), filed Sep. 30, 2021, which is a continuation of U.S. patent application Ser. No. 16/834,989 filed Mar. 30, 2020 (now U.S. Pat. No. 11,140,943), which is a continuation of U.S. patent application Ser. No. 16/525,875 filed Jul. 30, 2019 (now U.S. Pat. No. 10,645,991), which is a continuation of U.S. patent application Ser. No. 15/972,959 filed May 7, 2018 (now U.S. Pat. No. 10,376,015), which is a continuation of U.S. patent application Ser. No. 15/443,392 filed Feb. 27, 2017 (now U.S. Pat. No. 9,968,158), which is a continuation of U.S. patent application Ser. No. 14/298,454 filed Jun. 6, 2014 (now U.S. Pat. No. 9,578,927), which is a continuation of U.S. patent application Ser. No. 13/544,733 filed Jul. 9, 2012 (now U.S. Pat. No. 8,749,380), which is a continuation of U.S. patent application Ser. No. 13/034,311 filed Feb. 24, 2011 (now U.S. Pat. No. 8,217,788), which is a continuation of U.S. patent application Ser. No. 12/083,726 filed Apr. 16, 2008 (now U.S. Pat. No. 7,911,339), which is a 35 U.S.C. § 371 National Phase entry of International Patent Application No. PCT/US2006/040970 filed Oct. 18, 2006, which claims priority to U.S. Provisional Application No. 60/728,031 filed Oct. 18, 2005. All of these earlier applications are incorporated herein by reference.

BACKGROUND

Shoes (including sneakers or boots, for example) provide comfort and protection for feet. More importantly, shoes provide physical support for feet to reduce risk of foot injuries. A shoe is often necessary to provide support during intense physical activity, such as running, soccer and American football. As a shoe wears, physical support provided by the shoe decreases, thereby reducing associated protection from injury. When a critical wear level is reached, even if the shoe looks like it is not particularly worn, the shoe may not provide adequate support and may, in fact, cause damage to feet.

SUMMARY

In one embodiment, a shoe wear out sensor includes at least one detector for sensing a physical metric that changes as a shoe wears out, a processor configured to process the physical metric, over time, to determine if the shoe is worn out, and an alarm for informing a user of the shoe when the sole is worn out.

In another embodiment, a system determines the end of a shoe's life. Use of the shoe is sensed by at least one detector. A processor is configured to measure the use of the shoe and to determine if the shoe is worn out. An alarm informs a user of the shoe when the shoe is worn out.

In another embodiment, a body bar sensing system includes a housing with at least one detector for sensing a physical metric that indicates repeated movement of the housing when attached to the body bar, a processor configured to process the physical metric, over time, to determine repetitions thereof, and a display for informing a user of the repetitions.

In another embodiment, a system assesses activity and displaying a unitless activity value and includes a detector for sensing activity of a user of the system, a processor for processing sensed activity data from the detector, a display for displaying the unitless activity value, and an enclosure for housing the detector and the processor. The processor periodically reads the sensed activity data from the detector and processes the data to generate an activity number, the number being used to generate the unitless activity value based upon a maximum number and a display range.

In another embodiment, a method determines a unitless activity value for a desired period of activity. A period accumulator is cleared prior to the start of the activity period. A detector is periodically sampled to obtain data that is processed to determine a number representative of the sampling period. The number is added to the period accumulator. The unitless activity value is then determined based upon the period accumulator, a maximum activity number and a display range. The unitless activity value is then displayed. The sampling, processing and adding are repeated until data is sampled for the desired period of activity.

In another embodiment, a method assesses activity unitlessly by detecting motion of a user, processing the detected motion, over time, to determine an activity value, ratioing the activity value to a maximum activity value, and reporting a scaled unitless activity value to the user based upon the ratio and a scale.

A software product has instructions, stored on computer-readable media, that, when executed by a computer, perform steps for determining a unitless activity value for a desired period of activity, including instructions for: detecting motion of a user, processing detected motion, over time, to determine an activity value, ratioing the activity value to a maximum activity value, and reporting a scaled unitless activity value to the user based upon the ratio and a scale.

DETAILED DESCRIPTION OF THE FIGURES

Figure 1:
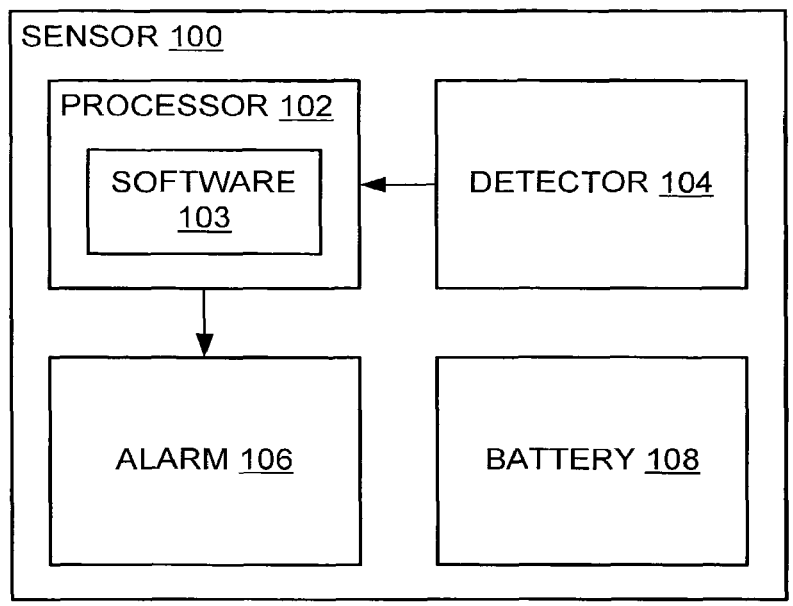
FIG. 1 shows one exemplary embodiment of a shoe wear-out sensor.

FIG. 1 shows one shoe-wear out sensor 100. Sensor 100 includes a processor 102, a detector 104 and an alarm 106.

A battery 108 may be used to power processor 102, detector 104 and alarm 106; alternatively, a magnetic coil generator (not shown) or other mechanical motion-to-electricity conversion device may be employed with sensor 100 to power these elements. Detector 104 is for example an accelerometer and/or a force sensing resistor (FSR). Alarm 106 is for example a light emitting diode (LED) and/or a small speaker and/or a small sound actuator (e.g., a buzzer, piezoelectric beeper etc).

Figure 2:
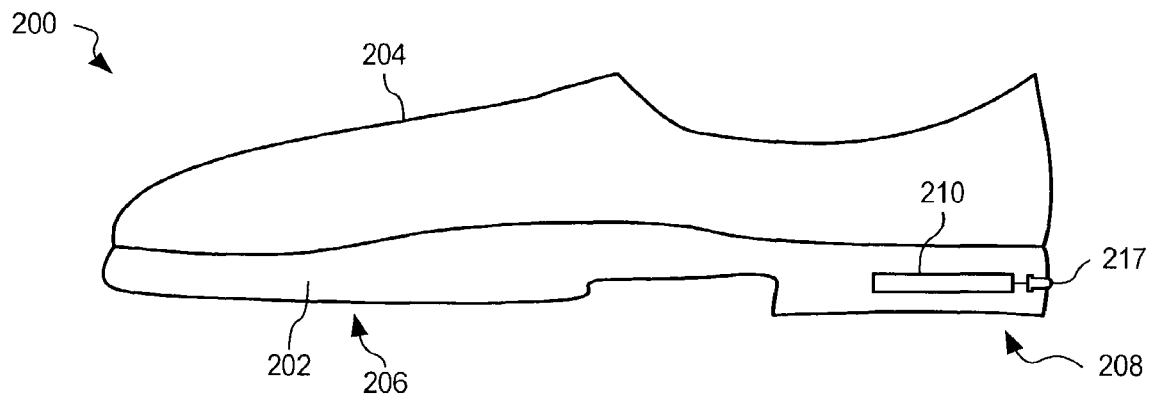
FIG. 2 shows one exemplary embodiment of a shoe with a shoe wear out sensor.

FIG. 2 shows a shoe 200 with a shoe-wear out sensor 210. Shoe 200 is for example a running or sport shoe, boot (e.g., a snowboard or hiking boot), slipper, dress shoe or flip-flop; shoe 200 may alternatively be an orthopedic shoe for providing special foot support. Sensor 210 may represent sensor 100, FIG. 1. In the illustrated embodiment, shoe 200 has a sole 202 and an upper part 204. Sole 202 has an outsole 206 and a heel 208. Sensor 210 is shown contained within heel 208; however sensor 210 may be placed elsewhere within or on the shoe to function similarly.

Figure 3:
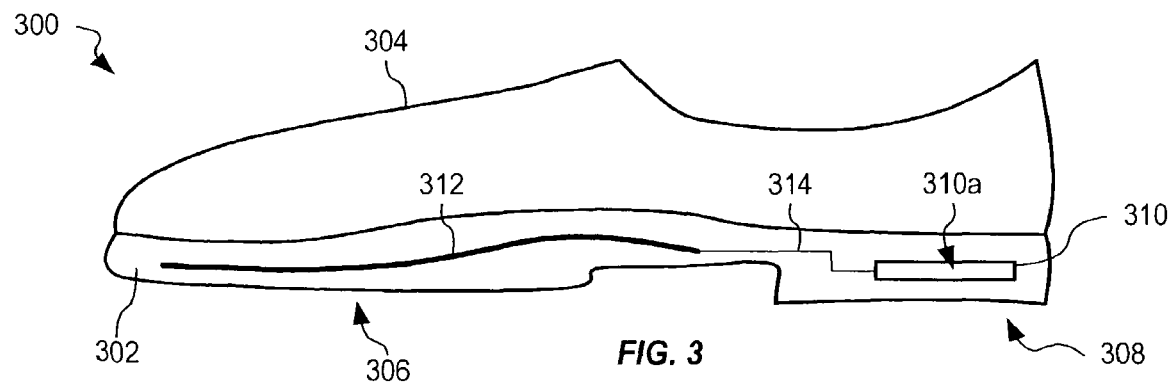
FIG. 3 shows another exemplary embodiment of a shoe with a shoe wear out sensor.

FIG. 3 shows one exemplary embodiment of a shoe with a shoe-wear out sensor 310. Sensor 310 may again represent sensor 100, FIG. 1. Shoe 300 is shown with a sole 302 and an upper part 304. Sole 302 has an outsole 306 and a heel 308. Shoe 300 may again represent, for example, a running shoe, sports shoe or orthopedic shoe (or other type of shoe or boot). Electronics 310a of sensor 310 are shown contained within heel 308; but detector 312 is shown located within outer sole 306, illustrating that the elements of sensor 100 (FIG. 1) may be dispersed to various locations of the shoe while providing similar functionality. Detector 312 is for example detector 104, FIG. 1; it may thereby be a force sensing resistor and/or a piezoelectric foil that is electrically connected, via connection 314, to electronics 310a of sensor 310. If detector 312 is a piezoelectric foil (or other piezoelectric device), use of shoe 300 results in flexing of detector 312 which may generate sufficient electricity to power electronics of sensor 310, avoiding the need for battery 108.

FIGS. 1, 2 and 3 are best viewed together with the following description. Sensor 100 may be embedded in a shoe (e.g., sensors 210, 310 within 20 shoes 200, 300) and configured to determine when that shoe has "worn out". It then informs the user, via alarm 106, that it is time to buy a new shoe (usually a new pair of shoes). In an embodiment, alarm 106 is an LED 217 that is positioned at the outside of the shoe such that it may be seen, when activated, by the user of the shoe, as illustratively shown in FIG. 2.

Processor 102 may operate under control of algorithmic software 103 (which is illustratively shown within processor 102, though it may reside elsewhere within sensor 100, for example as stand alone memory of sensor 100). Algorithmic software 103 for example includes algorithms for processing data from detector 104 to determine when a shoe is worn out.

Figure 4A:
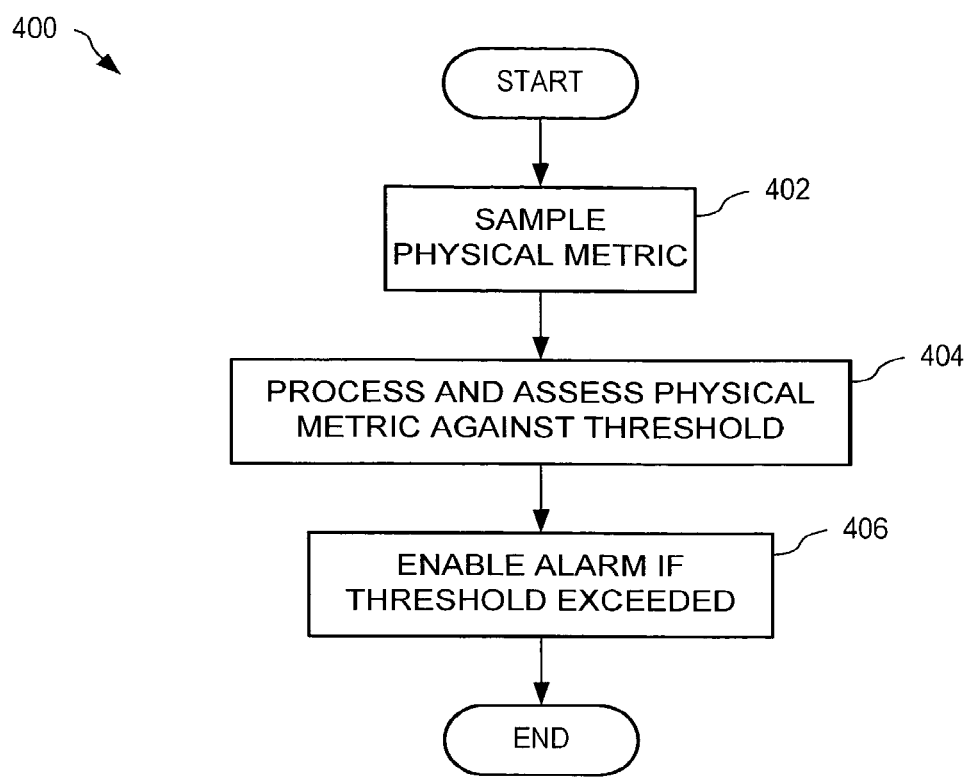
FIG. 4A shows one exemplary process for determining shoe wear out.

FIG. 4A for example illustrates one process 400 performed by processor 102 of FIG. 1. In step 402, processor 102 samples detector 104 to determine a physical metric associated with the shoe. In an example of step 402, detector 104 is an accelerometer a11d thereby provides acceleration data resulting from movement of the shoe upon a surface as the physical metric. For example, as the shoe strikes the ground when in use, processor 102 takes a plurality of samples using detector 104 to form an impact profile. In step 404, processor 102 processes the physical metric and compares it against a predetermined threshold, response curve or other data reference. In an example of step 404, processor 102 compares the impact profile determined from the accelerometer against an impact profile of a "new" shoe. In another example of steps 402, 404, the physical metric is power spectral density corresponding to certain frequencies of interest; and the power spectral density is compared, during use of the shoe, to a data reference containing power spectral density of a new or acceptably performing shoe. If the current data (i.e., physical metric) is too large or exceeds the data reference, for example, then processor 102 sets off alarm 106 (e.g., lights LED 217) in step 406. In one embodiment, upon first use of the shoe, processor 102 determines an impact profile of the new shoe that is then used (e.g., as the threshold or data reference) in comparison against subsequently determined impact profiles. Or, upon first use of the shoe, for example, processor 102 may store the appropriate data reference (e.g., power spectral density or threshold) for comparison against data captured in latter uses of the shoe. In this way, therefore, process 400 may be efficiently used to inform a user of shoe wear out.

As noted, data from detector 104 may be processed in the frequency domain (e.g., using Fourier transforms of data from detector 104) so as to evaluate, for example, power spectral density of the physical metric (e.g., acceleration or force), in step 404. In this manner, therefore, a range of frequencies may be evaluated (e.g., an area under the curve for certain frequencies may be integrated) from detector 104 and then compared to similar data (as the threshold) of a new shoe. As a shoe wears, the elasticity of the material from which it is made changes; thus the ability of the material to absorb the shock of the shoe contacting the ground deteriorates, resulting in more shock force being transferred to the foot within the shoe. By determining the increase of the shock force above the threshold, in this embodiment, the wear on the shoe may be determined.

We now specifically incorporate by reference the teachings and disclosure of: U.S. Pat. Nos. 6,539,336; 6,266,623; 6,885,971; 6,856,934; 6,8963,818; 6,499,000; and U.S. application Ser. No. 10/297,270. These patents and applications provide useful background, power sensing and weight/movement monitoring techniques suitable for use with the teachings of this present application.

In an embodiment, similar to the embodiment of FIG. 3, processor 102 determines wear of shoe 300 based upon weight of the user of shoe 300. By using signals from detector 312 to determine an approximate weight of the user of shoe 300 (for example by using a pressure sensor and fluid-filled cavity as detector 104), processor 102 may determine a life expectancy of shoe 300. Since the wear on the shoe is roughly proportional to the weight applied by the wearer, during activity, by determining the weight of the wearer and the amount the shoe is used (e.g., how often and how long the shoe is used), processor 102 may thus determine shoe wear with increased accuracy. That is, a shoe used by someone who spends most of their time sitting at a desk receives less wear that a shoe used by someone who spends most of the day standing on their feet.

In another embodiment, by sensing when the shoe is used—or for how long—the teachings herein may instead be applied so as to set off the alarm after a term or time of use has expired. For example, if a shoe is specified for use to at least 100 hours or 500 miles (or other similar metric specified by the shoe manufacturer), then by sensing weight or acceleration (or other physical metric, via detector 104) that use may be determined; processor 102 then activates alarm 106 when the use is exceeded. For example, using one or more accelerometers as detector 104, speed of the shoe may be determined through operation of processor 102 using an appropriate algorithm within software 103; this processor 102 then uses the speed information to determine distance traveled and sets off alarm 106 when, for example, the manufacturer's specified distance use is met. Illustratively, in another example, if the manufacturer specifies that the shoe may be used under normal conditions for 500 hours (or some other time), then detector 104 in the form of an accelerometer may determine when the shoe is in use; processor 102 then determines the period of use, over time (e.g., weeks and months) and sets off alarm 106 when the accumulated use exceeds the specified limit.

Figure 4B:
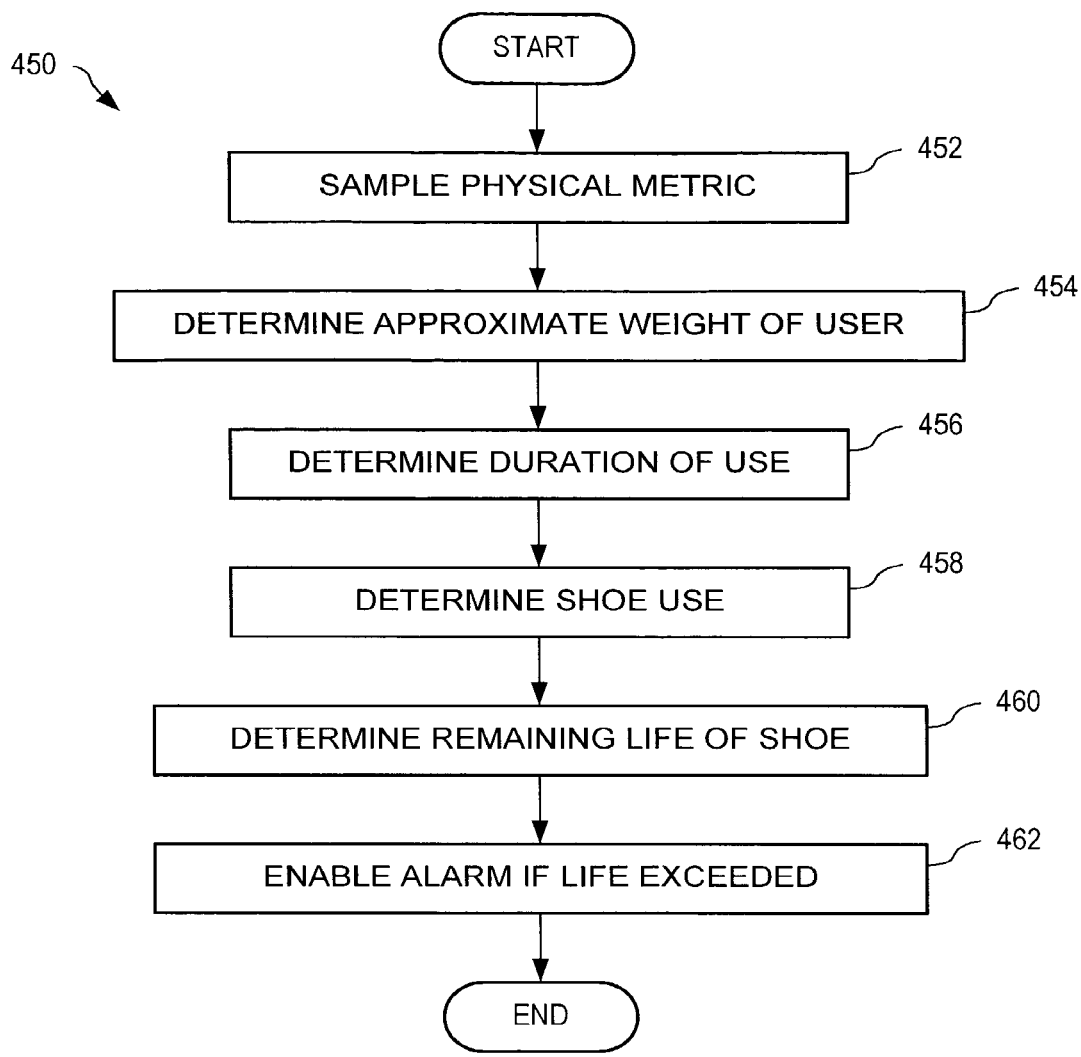
FIG. 4B shown one exemplary process for determining shoe wear out.

FIG. 4B for example illustrates one process 450 performed by processor 102 of FIG. 1 for determining shoe wear out. In step 452, processor 102 samples detector 104 to determine one or more physical metrics associated with the shoe. In an example of step 402, detector 104 includes a fluid filled cavity and a pressure sensor and thereby provides a signal representative of force upon the shoe (e.g., a value representative of the weight of the user of the shoe). For example, as the shoe is used, processor 102 takes a plurality of pressure reading from detector 104. In step 454, processor 102 determines an approximate weight upon the shoe based upon samples of step 452. In one example of step 454, processor 102 utilizes algorithms of software 103 to determine an approximate weight of the user of the shoe based upon pressure values sensed by detector 104. In step 456, processor 102 determines the duration of the shoe's use. In one example of step 456, processor 102 utilizes algorithms of software 103 to measure the duration that the shoe is used based upon readings from detector 104 and an internal timer of processor 102. In step 458, processor 102 determines the shoe use for the sample period of step 452. In one example of step 458, processor utilizes algorithms of software 103 to determine a use factor based upon the determined weight of step 454 and the duration of use of step 458. In step 460, processor 102 determines remaining life of the shoe based upon the determined shoe use of step 458. In one example of step 460, processor 102 maintains a cumulative value of usage determined in step 458 for comparison against a manufacturer's expected usage of the shoe. In step 462, processor 102 enables alarm 106 if the shoe's life is exceeded. Steps 452 through 462 repeat periodically throughout the life of the shoe to monitor shoe usage based upon wear determined from the weight of the user and the duration of use.

In the above description of process 450, it is not necessary that weight be determined. Rather, in an embodiment, it may instead be determined that the shoe is in "use" based on an algorithm using the pressure or force based detector 104; and then this use is accumulated time-wise to determine when the shoe's life expectancy is exceeded. For example, once a user puts weight onto this detector (in this embodiment), then processor 102 detects (through use of an algorithm as software 103) that the shoe is in use due to the presence of weight onto detector 104.

Figure 4C:
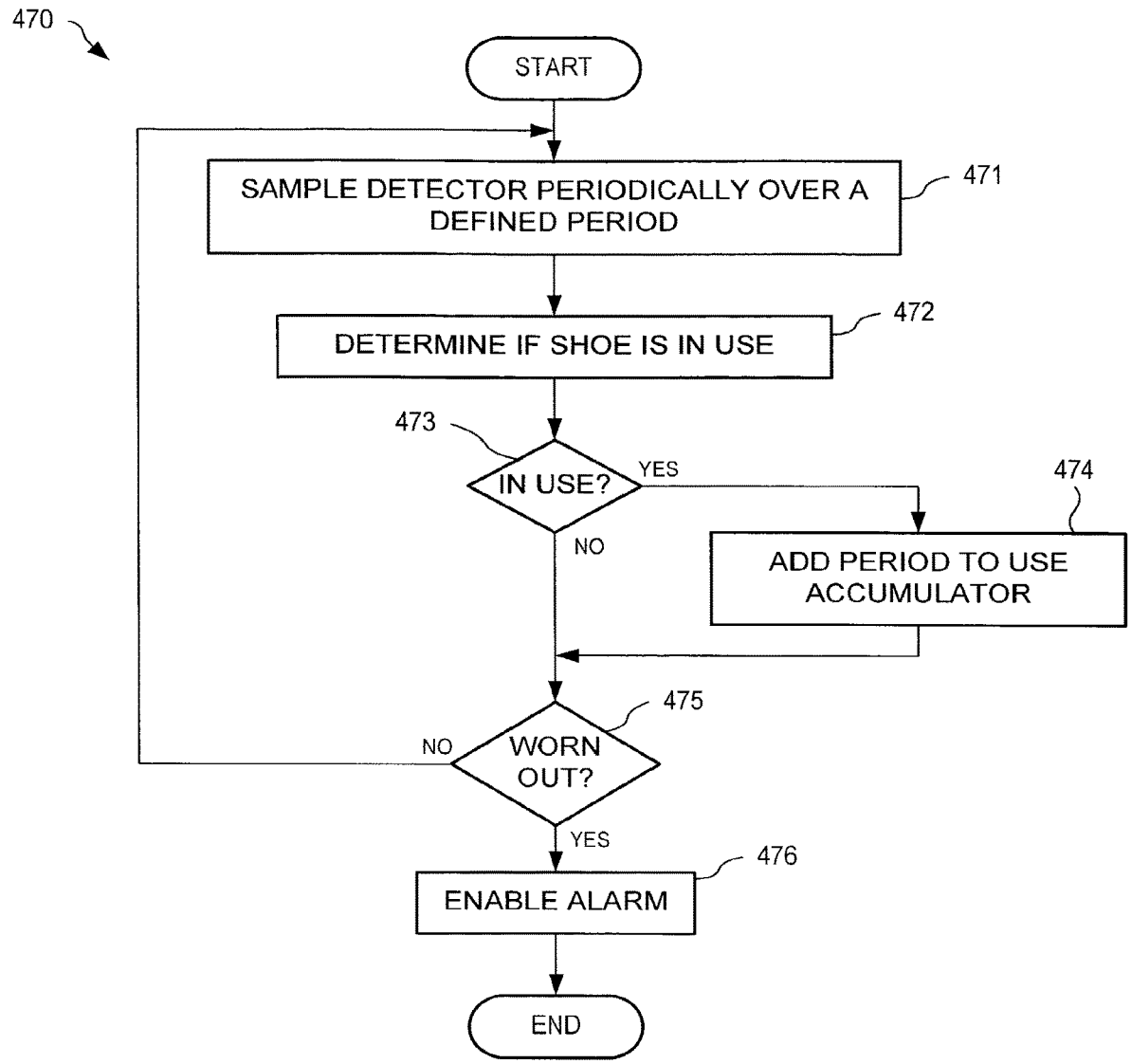
FIG. 4C shows one exemplary process for determining shoe wear out.

FIG. 4C for example illustrates one process 470 performed by processor 102 of FIG. 1 for determining shoe wear out. In step 471, processor 102 samples detector 104 periodically over a defined period. In one example of step 471, detector 104 is an accelerometer that is sampled periodically by processor 102 over a period of ten seconds. In step 472, processor 102 determines if the shoe is in use. In one example of step 472, processor 102 utilizes algorithms of software 103 to process the samples of step 471 to determine if the shoe is in use. Step 473 is a decision. If, in step 473, processor 102 determines that the shoe is in use, process 470 continues with step 474; otherwise process 470 continues with step 475. In step 474, processor 102 adds a value representative of the defined period of step 471 to an accumulator. In one example of step 474, a non-volatile accumulator is incremented by one, where the one represents a period of ten seconds. Step 475 is a decision. If, in step 475, processor 102 determines that the shoe is worn out, process 470 continues with step 476; otherwise process 470 continues with step 471. In one example of the decision of step 475, processor 102 compares the use accumulator of step 474 against a value representative of the expected life of the shoe. Steps 471 through 475 repeat throughout the lifetime of the shoe. As appreciated, power saving measures may be used within sensor 100 when it is determined that the shoe in which sensor 100 is installed is not in use. In step 476, processor 102 enables alarm 106. In one example of step 476, processor 102 may periodically activate LED 217, FIG. 2, until battery 108 is exhausted.

Process 470 thus determines the wear on a shoe by measuring the amount of use and comparing it against the expected use defined by a manufacturer, for example. In an embodiment, the use accumulator of step 474 is a timer within processor 102. This timer is started when step 473 determines that the shoe is in use and is stopped when step 473 determines that the shoe is not in use. This timer thus accumulates, in real time, the use of the shoe for comparison against a manufacturer's expected use. In another embodiment, step 472 may determine the number of steps a shoe has taken such that the use accumulator of step 474 accumulates the total number of steps taken by the shoe. This total number of steps is then compared to the manufacturer's recommended number of steps expected in the shoes life time.

Figure 4D:
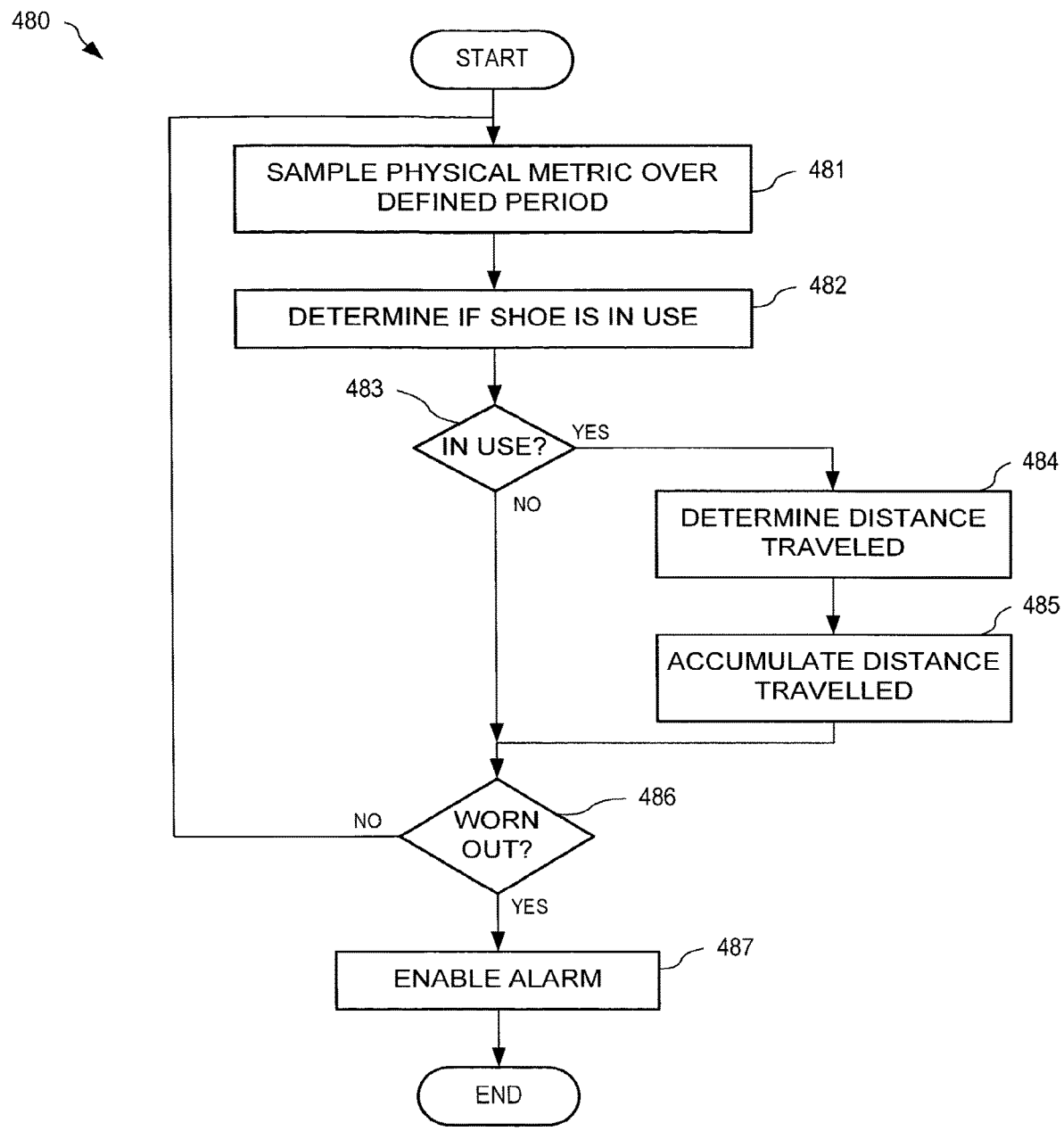
FIG. 4D shown one exemplary process for determining shoe wear out.

FIG. 4D illustrates one process 480 performed by processor 102 of FIG. 1 for determining shoe wear out. In step 481, processor 102 samples detector 104 periodically over a defined period. In one example of step 481, detector 104 is an accelerometer and processor 102 samples acceleration values over a period of 1 second. In step 482, processor 102 determines if the shoe is in use. In one example of step 482, processor 102 utilizes algorithms of software 103 to determine if characteristics of samples values of step 481 indicate that the shoe is in use. Step 483 is a decision. If, in step 483, processor 102 determines that the shoe is in use, process 480 continues with step 484; otherwise process 480 continues with step 486. In step 484, processor 102 determines a distance traveled over the defined period of step 481. In one example of step 484, processor 102 utilizes algorithms of software 103 to first determine speed of the shoe, and then determines distance covered in one second. In step 485, processor 102 accumulates the distance traveled. In one example of step 485, processor 102 adds the distance determined in step 484 to a total distance traveled accumulator. In one example, this accumulator is stored in non-volatile memory. Step 486 is a decision. If, in step 486, processor 102 determines that the shoe is worn out, process 480 continues with step 487; otherwise process 480 continues with step 481. In one example of step 486, processor 102 compares the total accumulated distance of step 485 against the manufacturer's recommended maximum distance for the shoe. Steps 481 through 486 repeat throughout the lifetime of the shoe. As appreciated, power saving measures may be used within sensor 100 when it is determined that the shoe is not in use. In step 487, processor 102 enables alarm 106. In one example of step 487, processor 102 may periodically activate LED 217, FIG. 2, until battery 108 is exhausted. Process 480 thus determines shoe wear by measuring the distance traveled by the shoe, using one or more accelerometers, and compares that distance to a manufacturer's recommended maximum distance for the shoe.

Figure 5:
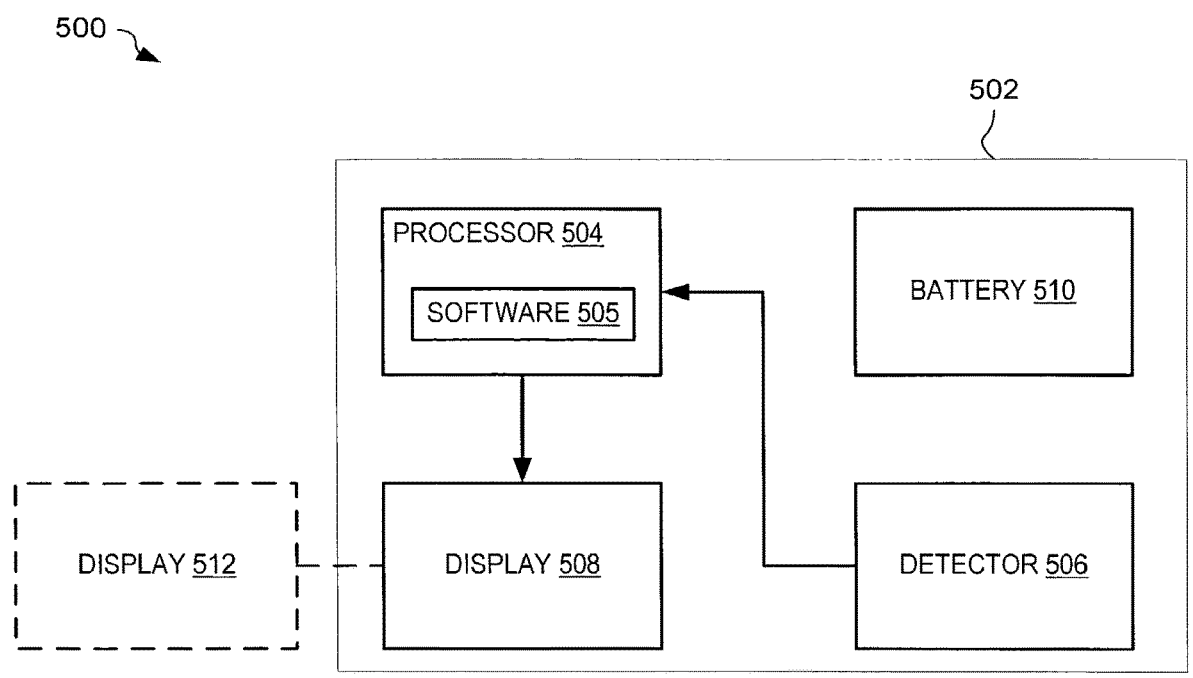
FIG. 5 shows one body bar sensing system embodiment.

FIG. 5 shows a body bar sensing system 500. System 500 includes a housing 502, a processor 504, a detector 506 and either an internal display 508 or an external display 512. A battery 510 may be used to power processor 504, detector 506 and display 508/512. Detector 506 is for example an accelerometer or a Hall Effect sensor. Display 508/512 is for example a liquid crystal display and/or a small speaker (e.g., that emits voice annunciations or other sounds generated by processor 504).

Figure 6:
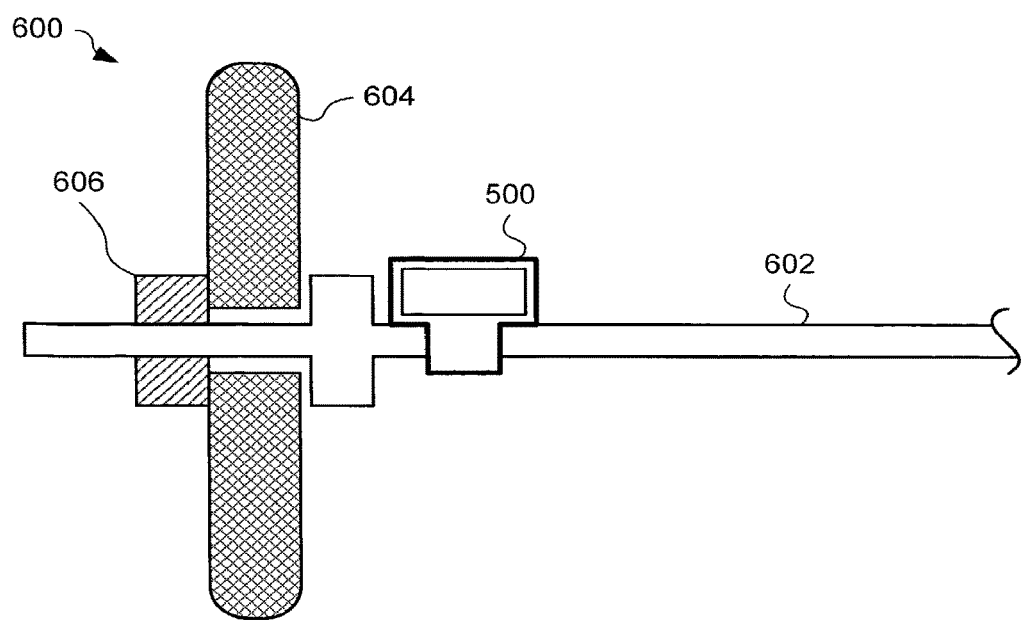
FIG. 6 shows one part of an exemplary body bar with a body bar sensing system embodiment attached.
Figure 7:
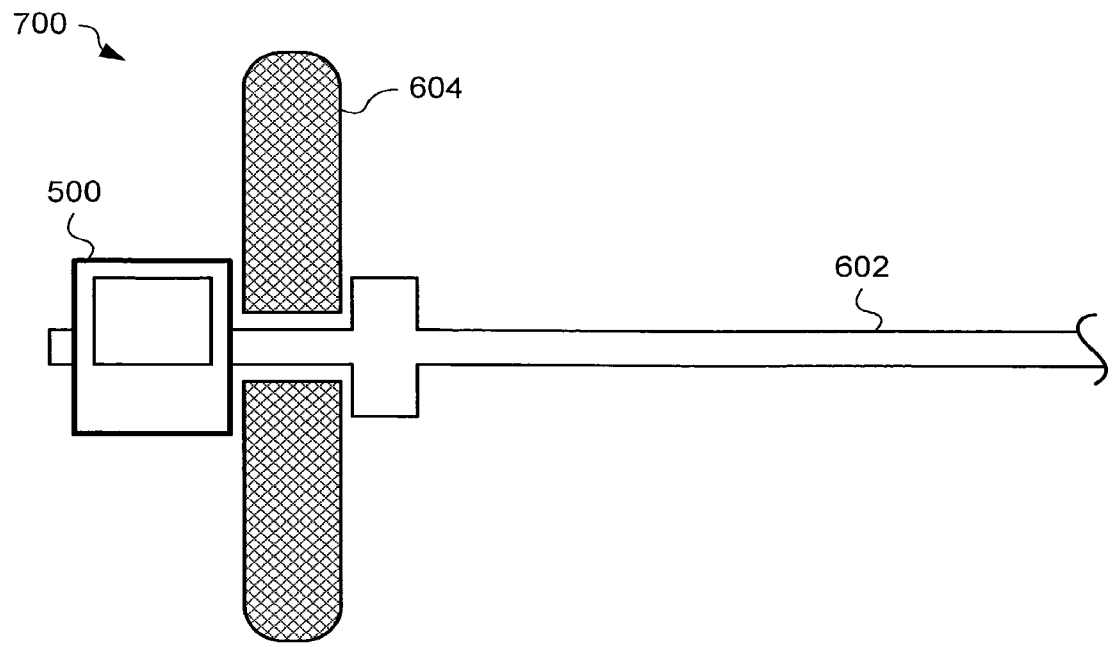
FIG. 7 shows one part of a body bar in an embodiment showing a weight and a body bar sensing system that secures the weight onto the body bar.

FIG. 6 shows one part of an exemplary body bar 602 with body bar sensing system 500 attached; a weight 604 and a retaining clip 606 are also shown to secure weight 604 onto body bar 602 (note, some body bars use no weights but weight is shown in FIG. 6 for illustrative purposes). Body bar 602 may represent a work out bar used by people in the gym, or a barbell, or other similar apparatus that requires a number of repetitions in exercise. FIG. 7 shows body bar 602 in an embodiment with another body bar sensing system 500 that secures weight 604 onto body bar 602. That is, sensing system 500 in addition operates as retaining clip 606, FIG. 6.

FIGS. 5, 6 and 7 are best viewed together with the following description. Housing 502 attaches to body bar 602 as shown in FIG. 6 or as shown in FIG. 7. Processor 504 utilizes detector 506 to determine when system 500 (as attached to body bar 602) has performed one repetition; it then informs the user, via display 508/512 for example, of a number of repetitions (or whether the user has performed the right number or any other number of planned repetitions as programmed into processor 504).

Where display 512 is used (i.e., remote from housing 502), a wireless transmitter (not shown) may be included within housing 502 to remotely provide data from processor 504 to remote display 512 (as shown in dotted outline). Where display 508 is integral with housing 502, then display 508 provides a visual display for a user when housing 502 attaches to the body bar. In one embodiment, display 512 (shown in dotted outline) is part of a watch (or a MP3 player or a cell phone) that may be seen when worn or used by the user when performing exercises; and measurements determined by processor 504 are transmitted to the watch (or to the MP3 player or cell phone) for display upon display 512.

Processor 504 may operate under control of algorithmic software 505 (which is illustratively shown within processor 504 although it may reside elsewhere within housing 502, such as stand alone memory within housing 502). Algorithmic software 505 for example includes algorithms for processing data from detector 506 to determine the repetitions performed by a user of body bar 602.

Figure 8:
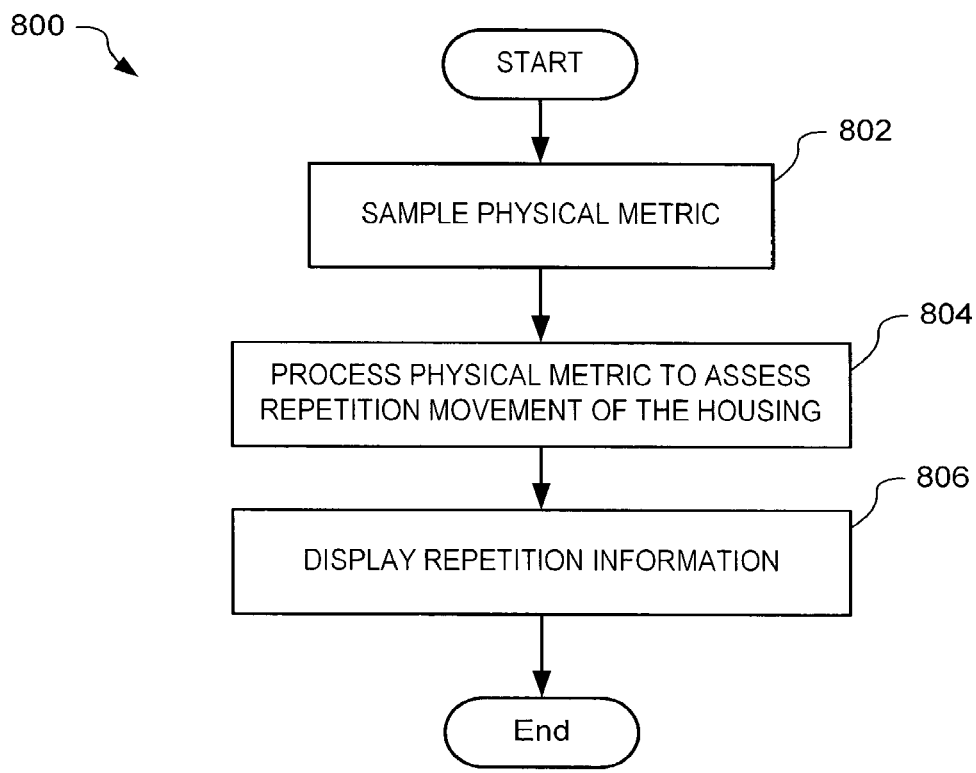
FIG. 8 shows one exemplary process for reporting body bar usage.

FIG. 8 shown one exemplary process 800 performed by processor 504. In step 802, detector 506 samples a physical metric associated with body bar 602. In an example of step 802, detector 506 is an accelerometer and thereby provides acceleration as the physical metric. In another example of step 802, detector is a Hall effect sensor which detects inversion (and thus repetition) of bar 602. In step 804, processor 504 processes the physical metric to assess whether the metric indicates a repetition of body bar 602. In an example of step 804, processor 504 evaluates the acceleration to determine if body bar 602 has been raised or lowered within a certain time interval. In step 806, repetition information is displayed to the user. In an example of step 806, the number of repetitions is relayed remotely (wirelessly) to a watch that includes display 512. That watch may also include a processor to store data and inform the user of repetitions for workouts, over time.

Figure 9:
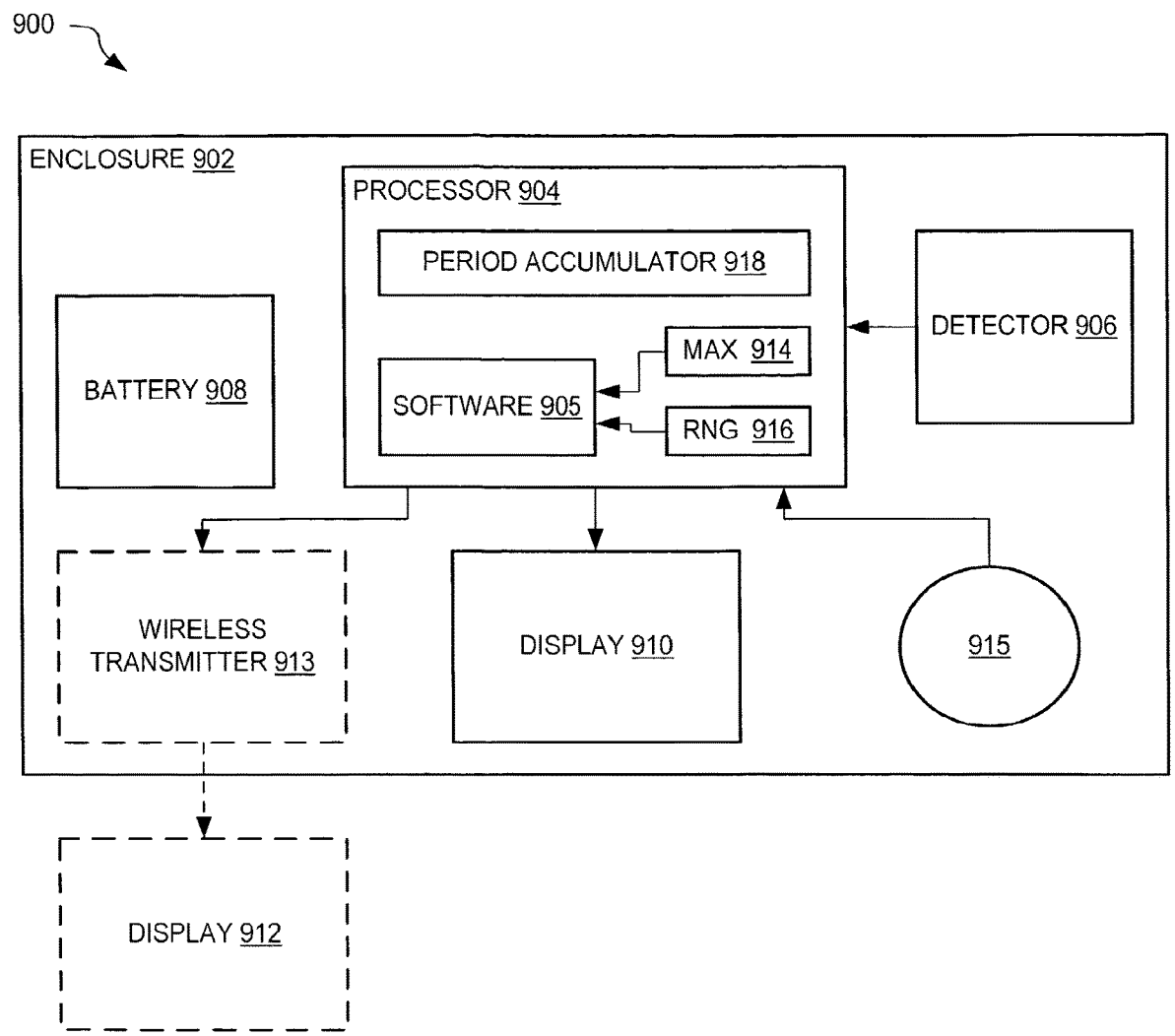
FIG. 9 shows an embodiment of a sensor that unitlessly assesses activity.

FIG. 9 shows one exemplary system 900 for unitlessly assessing activity of a user. System 900 has a processor 904, a detector 906 and a battery 908 within an enclosure 902 (e.g., a plastic housing). System 900 may include a display 910 for displaying unitless units to the user. Alternatively (or in addition), a remote display 912 is used to display the unitless units; in this case, enclosure 902 includes a wireless transmitter 913 in communication with, and controlled by, processor 904, so that transmitted unitless assessment numbers are sent to remote display 912.

In an embodiment, detector 906 is an accelerometer and processor 904 determines a value representing an activity level of the user of system 900 for display on display 910 or display 912. The accelerometer is for example positioned within housing 902 so that, when housing 902 is attached to a user, accelerometer 906 senses motion perpendicular to a surface (e.g., ground or a road or a floor) upon which the user moves (e.g., runs, dances, bounces). Data from the accelerometer is for example processed in the frequency domain as power spectral density (e.g., by frequency binning of the data). Multiple accelerometers (e.g., a triaxial accelerometer) may also be used as detector 906—for example to sense motion in other axes in addition to one perpendicular to the surface—and then processed together (e.g., in power spectral density domain) to arrive at a unitless value (as described below).

Processor 904 may utilize one or more algorithms, shown as software 905 within processor 904, for processing information obtained from detector 906 to assess the activity of the user. For example, processor 904 may periodically sample detector 906 to measure acceleration forces experienced by the user (when enclosure 902 is attached to the user, e.g., at the user's belt or shoe). Processor 904 may then process these forces to assess the activity level of the user. This activity level may represent effort exerted by the user when skiing.

The following represents a typical use of system 900, in an embodiment. In this example, detector 906 is one or more accelerometers. First, processor 904 determines when system 900 is in use, for example by sensing movement of housing 902 that corresponds to known activity (e.g., skiing or running). Alternatively, system 900 includes a button 915 that starts processing (in which case, separate determination of a known activity is not necessary). In an embodiment, button 915 is located proximate to display 912, and communicated wirelessly with processor 904. In this case, wireless transmitter 913 is a transceiver and button 915 includes a transmitter or a transceiver.

Once processor 904 knows (by sensing motion) or is notified (by button 915) that system 900 is operating in the desired activity, then it collects data over a period of that activity for example over 1 hour (a typical aerobic hour), 4 hours (a typical long run), 8 hours (a typical "ski" day) or over one full day, each of these being typical sport activity periods; however any time may be used and/or programmed in system 900. In an example, processor 904 integrates power spectral density of acceleration over this period of time to generate a number. This number in fact is a function of g's, frequency units and time, which does not make intuitive sense to the user. For example, consider a professional athlete who snowboards down difficult, double diamond terrain for eight hours. When system 900 measures his activity over this period, his number will be high (e.g., 500 "units" of power spectral density) because of his extreme physical capabilities. Then, when a less capable user uses system 900, a number of, e.g., 250 units may be generated because the user is not as capable (physically and skilled) as the professional. Therefore, in this example, an expected maximum number, shown as MAX 914 within processor 904, may be set at 500. A display range, shown as RNG 916 within processor 904, may also be defined such that system 900 may display a unitless value that is relative to the maximum number. Continuing with the above example, if RNG 916 is set to 100, system 900 displays a unitless value of 100 for the professional athlete and a unitless value of 50 for the less capable user (i.e., the less capable user has a 50% value of the professional athlete). By setting RNG 916 to other values, the displayed output range of system 900 may be modified.

In one example of use, system 900 is formed as a wrist watch to facilitate attachment to a child's wrist. System 900, when worn by the child, may then determine the child's activity level for the day. In another example of use, system 900 may be attached to a person's limb that is recuperating from injury (e.g., sporting injury, accident and/or operation etc.) such that system 900 may determine if the limb is receiving the right amount of activity to expedite recovery.

In another example of use, two skiers each use a system 900 when skiing for a day. The first skier, who is experienced and athletic, skis difficult ski runs (e.g., black double diamonds) all day, whereas the second skier is less experienced and skis easy runs (e.g., green runs) all day. At the end of the day, the first skier has a unitless activity value of 87 and the second skier has a unitless activity value of 12. Thus, these unitless activity values indicate the relative activity levels of each skier.

Figure 10:
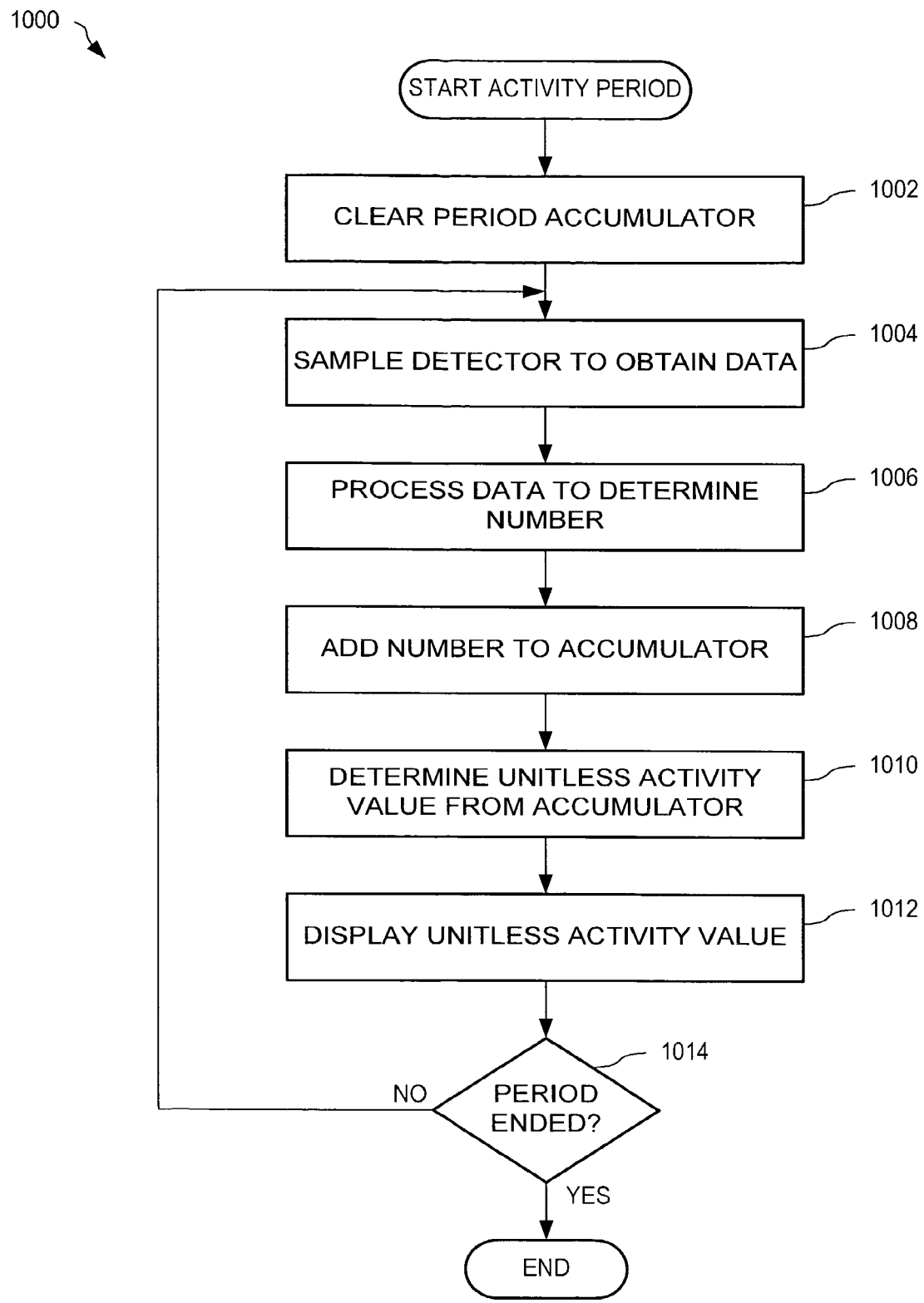
FIG. 10 shows a process for unitlessly determining activity.

FIG. 10 shows a flowchart illustrating one process 1000 for determining and displaying a unitless value representative of a users activity. Process 1000 may represent algorithms within software 905 of FIG. 9, for example, to be executed by processor 904. In step 1002, process 1000 clears a period accumulator. In one example of step 1002, processor 904, under control of software 905, clears period accumulator 918. In step 1004, process 1000 samples the detector to obtain data. In one example of step 1004, processor 904 periodically samples detector 906 over a sample period to determine data representative of the user's activity for that period. In step 1006, process 1000 processes the data of step 1004 to determine a number. In one example of step 1006, processor 904 integrates power spectral density of acceleration sampled in step 1004 over the sample period of step 1004 to generate a number. In step 1008, the number determined in step 1004 is added to the period accumulator. In one example of step 1006, processor 904 adds the number determined in step 1004 to period accumulator 918. In step 1010, process 1000 determines a unitless activity value from the accumulator. In one example of step 1010, processor 904 converts the accumulated value to a display value based upon MAX 914 and RNG 916. In step 1012, process 1000 displays the determined unitless activity value. In one example of step 1012, processor 904 sends the determined unitless activity value to display 912 via wireless transmitter 913. Step 1014 is a decision. If, in step 1014, the activity period for display has ended, process 1000 terminates; otherwise process 1000 continues with step 1004. Steps 1004 through 1014 thus repeat until the desired activity period is over.

Changes may be made to this application without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A wearable device comprising:
an input device configured to receive a first input, wherein the first input initiates a collection of data, wherein the data changes as a function of activity over time;
one or more sensors configured to detect the data during a detection period, wherein the detection period corresponds to an activity by a user of the wearable device performed after the first input;
processing circuitry configured to process the data detected during the detection period to determine one or more parameters indicative of effort exerted during the activity during the detection period; and
a display configured to display the one or more parameters indicative of the effort exerted during the activity during the detection period relative to a predetermined maximum effort associated with the activity.

2. The wearable device of claim 1, wherein the input device comprises a button configured to initiate the detection period and wherein the first input comprises an interaction with the button by the user of the wearable device.

3. The wearable device of claim 1, wherein the input device is further configured to receive a second input.

4. The wearable device of claim 3, wherein the first input comprises a detection at the one or more sensors of the user performing the activity; and
wherein the second input comprises a detection at the one or more sensors of the user ceasing the activity.

5. The wearable device of claim 3, wherein a duration of the detection period corresponds to a duration between the first input and the second input.

6. The wearable device of claim 1, wherein the detection period is at least an hour.

7. The wearable device of claim 1, wherein the wearable device is configured to be worn on a wrist of the user during the detection period.

8. The wearable device of claim 1, wherein the one or more sensors include at least one accelerometer configured to detect one or more movements of the user associated with the activity performed by the user.

9. The wearable device of claim 8, wherein the one or more movements are indicative of a number of physical repetitions.

10. A method of detecting data corresponding to an activity performed by a user of a wearable device comprising an input device, one or more sensors, a display, and processing circuitry, the method comprising:
detecting, with the input device, a first input to initiate a detection period;
detecting, with the one or more sensors, the data associated with an activity performed by the user during the detection period;
processing, with the processing circuitry, the detected data to determine one or more parameters indicative of effort exerted during the activity by the user for the detection period; and
displaying, with the display, the one or more parameters indicative of the effort exerted during the activity during the detection period relative to a predetermined maximum effort associated with the activity.

11. The method of claim 10, further comprising:
detecting, with the input device, a second input to cease the detection period.

12. The method of claim 10, further comprising:
scaling, with the processing circuitry, the one or more parameters indicative of the effort extended during the activity by the user against the predetermined maximum effort associated with the activity.

13. The method of claim 12, further comprising:
prior to the scaling, identifying a type of the activity based on the data of the user during the detection period; and
prior to the scaling, identifying the predetermined maximum effort for the detection period based on the identified type of activity.

14. The method of claim 13, wherein identifying the type of activity comprises detecting use of the input device.

15. The method of claim 10, further comprising repeating the detecting, the processing, the displaying for a plurality of consecutive detection periods.

16. A non-transitory computer readable storage medium storing instructions, which when executed by processing circuitry of a wearable device, cause the wearable device to:
detect, with an input device, a first input to initiate a detection period;
detect, with one or more sensors, data associated with an activity performed by a user during the detection period;
process, with the processing circuitry, the data to determine one or more parameters indicative of effort exerted during the activity by the user for the detection period; and
display, with the display, the one or more parameters indicative of the effort exerted during the activity by the user relative to a predetermined maximum effort associated with the activity.

17. The non-transitory computer readable storage medium of claim 16, wherein the instructions, when executed by the processing circuitry, further cause the wearable device to:
detect, with the input device, a second input to cease the detection period.

18. The non-transitory computer readable storage medium of claim 16, wherein the instructions, when executed by the processing circuitry, further cause the wearable device to:
scale, with the processing circuitry, the one or more parameters indicative of the effort extended during the activity by the user against the predetermined maximum effort associated with the activity.

19. The non-transitory computer readable storage medium of claim 16, wherein the instructions, when executed by the processing circuitry, further cause the wearable device to:
prior to scaling, identify a type of activity based on the data of the user during the detection period; and
prior to scaling, identify the predetermined maximum effort for the detection period based on the identified type of activity.

20. The non-transitory computer readable storage medium of claim 19, wherein identifying the type of activity comprises a detection of use of the input device.

* * * * *